United States Patent [19]

Shaber

[11] Patent Number: 5,087,635
[45] Date of Patent: Feb. 11, 1992

[54] ALPHA-ARYL-ALPHA-PHENYLETHYL-1H-1,2,4-TRIAZOLE-1-PROPANENITRILES

[75] Inventor: Steven H. Shaber, Horsham, Pa.

[73] Assignee: Rohm and Haas Company, Philadelphia, Pa.

[21] Appl. No.: 376,948

[22] Filed: Jul. 7, 1989

Related U.S. Application Data

[63] Continuation of Ser. No. 880,990, Jul. 2, 1986, abandoned.

[51] Int. Cl.$^5$ .................. A01N 43/653; C07D 249/08
[52] U.S. Cl. .................................. 514/383; 514/184; 548/101; 548/267.4
[58] Field of Search .................. 548/101, 262, 267.4; 514/184, 383

[56] References Cited

U.S. PATENT DOCUMENTS 4,365,165  12/1982  Miller et al. ................. 514/383
4,507,140   3/1985  Sugavanum ................. 71/76

FOREIGN PATENT DOCUMENTS 0052424   5/1982  European Pat. Off. ......... 548/262
  61840  10/1982  European Pat. Off. ......... 548/262
  63099  10/1982  European Pat. Off. ......... 548/262
2119374  11/1983  United Kingdom ............ 548/262

OTHER PUBLICATIONS

Mitsudera et al., Synthesis and Fungicital Acpuitic of 1,2,4 Triazole Derivatives; J. Takeda Res. Lab., vol. 41, No. 3/4, 1982, pp. 148-153.
CA 100(7): 51587 Skoetsch et al., (Schering AG-DE 3,216,301, 10/27/83).

*Primary Examiner*—Patricia L. Morris
*Attorney, Agent, or Firm*—Polly E. Ramstad

[57] ABSTRACT

This invention relates to substituted and unsubstituted alpha-aryl-alpha-phenylethyl-1H-1,2,4-triazole-1-propanenitriles, their enantiomorphs, acid addition salts and metal salt complexes. These compounds, enantiomorphs, salts and complexes are highly active broad-spectrum systemic fungicides effective in controlling phytopathogenic fungi such as corn helminthosporium, barley helminthosporium, cucumber downy mildew, cucumber powdery mildew, cucumber anthracnose, botrytis, tomato early blight, tomato late blight, grape downy mildew, bean powdery mildew, peanut cercospora, rice blast, rice sheath blight, wheat leaf rust, wheat septoria nodorum, wheat powdery mildew and wheat stem rust. The invention also concerns a method of preparing alpha-aryl-alpha-triazolylmethylacetonitrile compounds by reacting an aryl-acetonitrile compound with a halomethyltriazole.

25 Claims, No Drawings

ALPHA-ARYL-ALPHA-PHENYLETHYL-1H-1,2,4-TRIAZOLE-1-PROPANENITRILES

This application is a continuation of application Ser. No. 880,990, filed July 2, 1986, now abandoned.

BACKGROUND OF THE INVENTION

This invention relates to alpha-aryl-alpha-phenylethyl-1H-1,2,4-triazole-1-propanenitriles and their use in controlling phytopathogenic fungi. The phenethyl and aryl moieties may be substituted or unsubstituted.

Miller et al., U.S. Pat. No. 4,366,165 discloses 1- and 4-arylcyanoalkyl-1,2,4-triazoles and their use against phytopathogenic fungi. However, neither the phenethyl triazoles of the present invention nor the benzyl triazoles were made by Miller et al. Therefore, they failed to recognize the particular class of compounds of the present invention or that this class has a particularly high degree of fungicidal activity. The phenethyl triazoles of the present invention are not only effective against wheat powdery mildew, wheat stem rust and wheat leaf rust but are significantly superior to the benzyl triazoles and phenyl triazoles against barley helminthosporium, rice blast and peanut early leafspot.

European Patent Application 52,424, published May 26, 1982, also generically discloses the compounds of the present invention. However, none of the present compounds were made. In fact, none of the examples of the 52,424 application have a cyano group attached to the quaternary carbon, but include either a hydroxy, methoxy, butoxy or allyloxy group. The three phenethyl triazole compounds which were made and disclosed in the 52,424 application are 4,4-dimethyl-3-hydroxy-3-(1,2,4-triazol-1-yl)methyl-1-(halogen substituted phenyl)-pentanes.

Published German patent application no. 3,216,301 discloses the fungicidal activity of alkoxytriazolepropionitriles.

European application 63,099 discloses the use of chloromethyltriazole to produce a 1H-1,2,4-triazol-1-yl-methylphosphonium salt.

Published British patent application 2,119,374 discloses a process to make alpha-(alkoxy, alkenoxy, alkynoxy or phenylalkoxy)-alpha-aryl-triazolylmethylacetonitrile compounds.

DESCRIPTION OF THE INVENTION

In accordance with the present invention, there is provided a new class of triazole propanenitriles which are alpha-aryl-alpha-phenylethyl-1H-1,2,4-triazole-1-propane-nitriles of the formula (I):

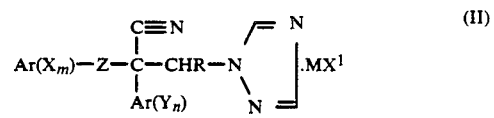

wherein Z is ethylene (—$CH_2CH_2$—), ethenylene (—CH=CH—), ethynylene (—C≡C—) or isopropylene

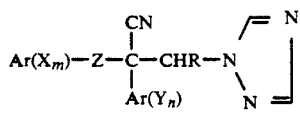

or halogenated ethylene, ethenylene or isopropylene; Ar ($X_m$) is a substituted or unsubstituted $C_6$-$C_{10}$ aromatic ring structure; Ar($Y_n$) is a substituted or unsubstituted aryl; X and Y are independently the same or different and are selected from halogen, alkyl optionally substituted with up to 3 halogens, alkenyl optionally substituted with up to 3 halogens, hydroxy, alkoxy, alkenoxy, phenyl optionally substituted with up to 2 halogens, cyano, amino, monoalkylamino, dialkylamino, —C(O)H, —C(O)$NR_1R_2$ wherein $R_1$ and $R_2$ are independently hydrogen or alkyl, and alkylsulfonyl; R is hydrogen or optionally substituted phenyl; and m and n are independently 0 to 3. The new class of triazole propanenitriles also includes the agronomically acceptable enantiomorphs, acid addition salts and metal complexes of formula (I).

The term "aryl" is meant to include $C_6$-$C_{10}$ aromatic ring structures, a five member aromatic ring having 4 carbon atoms and one nitrogen, oxygen or sulfur atom, or a six member aromatic ring having 1 or 2 nitrogen atoms and 5 or 4 carbon atoms, all optionally substituted with up to 3 halogens, trifluoromethyl or ($C_1$-$C_6$)alkyl;

The term "alkyl" is meant to include both branched and straight chained alkyl groups of carbon atoms, preferably $C_1$-$C_8$. Typical alkyl groups which are encompassed by the use of this term include methyl, ethyl, n-propyl, iso-propyl, n-butyl, sec-butyl, iso-butyl, tert-butyl, pentyl, neo-pentyl, iso-pentyl, hexyl, heptyl, iso-octyl and the like.

The term "alkoxy," as used in the present specification, is meant to include alkenoxy, as well as the radical consisting of an alkyl group bonded to an oxygen atom. The preferred groups include ($C_1$-$C_6$)alkoxy. Typical alkoxy groups which are encompassed by the use of the term include methoxy, ethoxy, propoxy, n-butoxy, iso-butoxy, pentoxy, hexoxy and allyloxy.

The term "alkylsulfonyl" means —$SO_aR'$ where a is 0, 1 or 2 and R' is an alkyl group. Preferably R' is $C_1$-$C_6$. The term "arylsulfonyl" means —$SO_aR''$ where a is 0, 1 or 2 and R" is aryl as defined above.

The acids which can be utilized in making the acid addition salts of the present invention include, for example, hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric and phthalic acids.

Another embodiment of this invention is the metal salt complexes of the formula (II):

$$Ar(X_m)-Z-\underset{\underset{Ar(Y_n)}{|}}{\overset{\overset{C\equiv N}{|}}{C}}-CHR-N\diagdown\underset{N=\!=}{\overset{=N}{\diagup}}\cdot MX^1 \quad (II)$$

wherein Z, Ar($Y_n$), X, Y, n and m are as defined in formula (I) above and M is a cation selected from Group IIA, IB, IIB, VIB, VIIB and VIII of the Periodic Table and $X^1$ is an anion selected so that the sum of the valence charges of the cation M and anion $X^1$ equal zero.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartrate, malate, maleate, fumarate, p-toluenesulfonate, methanesulfonate, mono- or di-(C$_1$–C$_4$)alkyldithiocarbamate, (C$_1$–C$_4$)alkylenebisdithiocarbamate and the like.

A preferred embodiment of this invention is the compounds, agronomically acceptable enantiomorphs, salts and complexes of formulas (I) and (II) wherein Z is ethylene, Ar is phenyl and X and Y are hydrogen, halogen or trifluoromethyl. A more preferred embodiment of this invention is where $Y_n$ is hydrogen, 2-alkoxy, 4-halo or 3-trifluoromethyl and X is a hydrogen, 4-halo or 4-trifluoromethyl. Another preferred embodiment is where Y is 2-halo and X is 4-halo or Y is 4-halo and X is 2-halo. In yet another preferred embodiment, X is 3-halo and Y is hydrogen.

Typical compounds encompassed by the present invention which were made include the following:

1. alpha-(4-chlorophenyl)-alpha-(2-phenylethyl)-1H-1,2,4-triazole-1-propanenitrile
2. alpha-phenyl-alpha-(2-phenylethyl)-1H-1,2,4-triazole-1-propanenitrile
3. alpha-(2-methoxyphenyl)-alpha-(2-phenylethyl)-1H-1,2,4-triazole-1-propanenitrile
4. alpha-(4-fluorophenyl)-alpha-(2-phenylethyl)-1H-1,2,4-triazole-1-propanenitrile
5. alpha-(2,4-dichlorophenyl)-alpha-(2-phenylethyl)-1H-1,2,4-triazole-1-propanenitrile
6. alpha-(4-chlorophenyl)-alpha-[2-(4-chlorophenyl)ethyl]-1H-1,2,4-triazole-1-propanenitrile
7. alpha-(4-chlorophenyl)-alpha-[2-(4-fluorophenyl)ethyl]-1H-1,2,4-triazole-1-propanenitrile
8. alpha-(4-chlorophenyl)-alpha-[2-(4-methylphenyl)ethyl]-1H-1,2,4-triazole-1-propanenitrile
9. alpha-(4-chlorophenyl)-alpha-[2-(4-methoxyphenyl)ethyl]-1H-1,2,4-triazole-1-propanenitrile
10. alpha-[2-(4-chlorophenyl)ethyl]-alpha-phenyl-1H-1,2,4-triazole-1-propanenitrile
11. alpha-[2-(4-fluorophenyl)ethyl]-alpha-phenyl-1H-1,2,4-triazole-1-propanenitrile
12. alpha-(2-phenylethyl)-alpha-(4-phenylphenyl)-1H-1,2,4-triazole-1-propanenitrile
13. alpha-phenyl-alpha-[2-(2-trifluoromethylphenyl)ethyl]-1H-1,2,4-triazole-1-propanenitrile
14. alpha-phenyl-alpha-[2-(3-trifluoromethylphenyl)ethyl]-1H-1,2,4-triazole-1-propanenitrile
15. alpha-[2-(2,4-dichlorophenyl)ethyl]-alpha-phenyl-1H-1,2,4-triazole-1-propanenitrile
16. alpha-[2-(4-bromophenyl)ethyl]-alpha-phenyl-1H-1,2,4-triazole-1-propanenitrile
17. alpha-[2-(2-chlorophenyl)ethyl]-alpha-phenyl-1H-1,2,4-triazole-1-propanenitrile
18. alpha-[2-(3-chlorophenyl)ethyl]-alpha-phenyl-1H-1,2,4-triazole-1-propanenitrile
19. alpha-phenyl-alpha-[2-(4-trifluoromethylphenyl)ethyl]-1H-1,2,4-triazole-1-propanenitrile
20. alpha-(4-chlorophenyl)-alpha-[2-(3-trifluoromethylphenyl)ethyl]-1H-1,2,4-triazole-1-propanenitrile
21. alpha-(4-fluorophenyl)-alpha-[2-(3-trifluoromethylphenyl)ethyl]-1H-1,2,4-triazole-1-propanenitrile
22. alpha-[2-(4-bromophenyl)ethyl]-alpha-(4-chlorophenyl)-1H-1,2,4-triazole-1-propanenitrile
23. alpha-(4-chlorophenyl)-alpha-[2-(4-trifluoromethylphenyl)ethyl]-1H-1,2,4-triazole-1-propanenitrile
24. alpha-(4-fluorophenyl)-alpha-[2-(4-trifluoromethylphenyl)ethyl]-1H-1,2,4-triazole-1-propanenitrile
25. alpha-[2-(4-bromophenyl)ethyl]-alpha-(4-fluorophenyl)-1H-1,2,4-triazole-1-propanenitrile
26. alpha-[2-(4-chlorophenyl)ethyl]-alpha-(4-fluorophenyl)-1H-1,2,4-triazole-1-propanenitrile
27. alpha-[2-(3-bromophenyl)ethyl]-alpha-phenyl-1H-1,2,4-triazole-1-propanenitrile
28. alpha-(4-fluorophenyl)-alpha-[2-(4-fluorophenyl)ethyl]-1H-1,2,4-triazole-1-propanenitrile
29. alpha-(2-methoxyphenyl)-alpha-[2-(4-trifluoromethylphenyl)ethyl]-1H-1,2,4-triazole-1-propanenitrile
30. alpha-[2-(3-chlorophenyl)ethyl]-alpha-(4-fluorophenyl)-1H-1,2,4-triazole-1-propanenitrile
31. alpha-(4-chlorophenyl)-alpha-[2-(3-chlorophenyl)ethyl]-1H-1,2,4-triazole-1-propanenitrile
32. alpha-(4-bromophenyl)-alpha-(2-phenylethyl)-1H-1,2,4-triazole-1-propanenitrile
33. alpha-(4-bromophenyl)-alpha-[2-(4-fluorophenyl)ethyl]-1H-1,2,4-triazole-1-propanenitrile
34. alpha-(3-chlorophenyl)-alpha-(2-phenylethyl)-1H-1,2,4-triazole-1-propanenitrile
35. alpha-(3-chlorophenyl)-alpha-[2-(4-chlorophenyl)ethyl]-1H-1,2,4-triazole-1-propanenitrile
36. alpha-(3-chlorophenyl)-alpha-[2-(4-fluorophenyl)ethyl]-1H-1,2,4-triazole-1-propanenitrile
37. alpha-(4-bromophenyl)-alpha-[2-(4-chlorophenyl)ethyl]-1H-1,2,4-triazole-1-propanenitrile
38. alpha-[2-(3-bromophenyl)ethyl]-alpha-(4-fluorophenyl)-1H-1,2,4-triazole-1-propanenitrile
39. alpha-[2-(3-bromophenyl)ethyl]-alpha-(4-chlorophenyl)-1H-1,2,4-triazole-1-propanenitrile
40. alpha-(2-chlorophenyl)-alpha-[2-(4-chlorophenyl)ethyl]-1H-1,2,4-triazole-1-propanenitrile
41. alpha-[2-(4-chlorophenyl)ethyl]-alpha-(2-fluorophenyl)-1H-1,2,4-triazole-1-propanenitrile
42. alpha-(4-chlorophenyl)-alpha-[2-(2-fluorophenyl)ethyl]-1H-1,2,4-triazole-1-propanenitrile
43. alpha-(4-fluorophenyl)-alpha-[2-(2-fluorophenyl)ethyl]-1H-1,2,4-triazole-1-propanenitrile
44. alpha-(2-chlorophenyl)-alpha-[2-(4-fluorophenyl)ethyl]-1H-1,2,4-triazole-1-propanenitrile
45. alpha-(2-fluorophenyl)-alpha-[2-(4-fluorophenyl)ethyl]-1H-1,2,4-triazole-1-propanenitrile
46. alpha-[2-(4-chlorophenyl)ethyl]-alpha-(3-trifluorophenyl)-1H-1,2,4-triazole-1-propanenitrile
47. alpha-[2-(4-chlorophenyl)ethyl]-alpha-(3-fluorophenyl)-1H-1,2,4-triazole-1-propanenitrile
48. alpha-(2-bromophenyl)-alpha-[2-(4-chlorophenyl)ethyl]-1H-1,2,4-triazole-1-propanenitrile
49. alpha-[2-(4-chlorophenyl)ethyl]-alpha-(2-methoxyphenyl)-1H-1,2,4-triazole-1-propanenitrile
50. alpha-(2-phenylethyl)-alpha-(3-trifluoromethylphenyl)-1H-1,2,4-triazole-1-propanenitrile
51. alpha-(3-trifluoromethylphenyl)-alpha-[2-(3-trifluoromethylphenyl)ethyl]-1H-1,2,4-triazole-1-propanenitrile
52. alpha-(3-fluorophenyl)-alpha-(2-phenylethyl)-1H-1,2,4-triazole-1-propanenitrile
53. alpha-(3-chlorophenyl)-alpha-[2-(3-trifluoromethylphenyl)ethyl]-1H-1,2,4-triazole-1-propanenitrile
54. alpha-(2-bromophenyl)-alpha-(2-phenylethyl)-1H-1,2,4-triazole-1-propanenitrile
55. alpha-(2-bromophenyl)-alpha-[2-(3-trifluoromethylphenyl)ethyl]-1H-1,2,4-triazole-1-propanenitrile
56. alpha-(3-fluorophenyl)-alpha-[2-(3-trifluoromethylphenyl)ethyl]-1H-1,2,4-triazole-1-propanenitrile
57. alpha-(2-chlorophenyl)-alpha-[2-(3-trifluoromethylphenyl)ethyl]-1H-1,2,4-triazole-1-propanenitrile
58. alpha-[2-(2-methoxyphenyl)ethyl]-alpha-phenyl-1H-1,2,4-triazole-1-propanenitrile
59. alpha-[2-(3-methoxyphenyl)ethyl]-alpha-phenyl-1H-1,2,4-triazole-1-propanenitrile 60. alpha-[2-(3,4-dimethoxyphenyl)ethyl]-alpha-phenyl-1H-1,2,4-triazole-1-propanenitrile
61. alpha-[2-(4-chlorophenyl)ethyl]-alpha-(4-methoxyphenyl)-1H-1,2,4-triazole-1-propanenitrile
62. alpha-(4-methoxyphenyl)-alpha-(2-phenylethyl)-1H-1,2,4-triazole-1-propanenitrile
63. alpha-(2-chloro-6-fluorophenyl)-alpha-(2-phenylethyl)-1H-1,2,4-triazole-1-propanenitrile
64. alpha-(2-chloro-6-fluorophenyl)-alpha-[2-(4-chlorophenyl)ethyl]-1H-1,2,4-triazole-1-propanenitrile
65. alpha-[2-(4-chlorophenyl)ethyl]-alpha-(2,6-dichlorophenyl)-1H-1,2,4-triazole-1-propanenitrile
66. alpha-[2-(3-bromophenyl)ethyl]-alpha-(3-chlorophenyl)-1H-1,2,4-triazole-1-propanenitrile
67. alpha-[2-(4-bromophenyl)ethyl]-alpha-(3-chlorophenyl)-1H-1,2,4-triazole-1-propanenitrile
68. alpha-[2-(3-bromophenyl)ethyl]-alpha-(3-fluorophenyl)-1H-1,2,4-triazole-1-propanenitrile
69. alpha-[2-(4-bromophenyl)ethyl]-alpha-(3-fluorophenyl)-1H-1,2,4-triazole-1-propanenitrile
70. alpha-phenyl-alpha-(2-phenyl)propyl-1H-1,2,4-triazole-1-propanenitrile
71. alpha-(3-fluorophenyl)-alpha-[2-(4-fluorophenyl)ethyl]-1H-1,2,4-triazole-1-propanenitrile
72. alpha-[2-(4-fluorophenyl)ethyl]-alpha-(3-trifluoromethylphenyl)-1H-1,2,4-triazole-1-propanenitrile
73. alpha-[2-(1-naphthyl)ethyl]-alpha-phenyl-1H-1,2,4-triazole-1-propanenitrile
74. alpha-[2-(4-bromophenyl)ethyl]-alpha-(2-ethoxyphenyl)-1H-1,2,4-triazole-1-propanenitrile
75. alpha-[2-(4-bromophenyl)ethyl]-alpha-(3-trifluoromethylphenyl)-1H-1,2,4-triazole-1-propanenitrile
76. alpha-(2-ethoxyphenyl)-alpha-[2-(3-trifluoromethylphenyl)ethyl]-1H-1,2,4-triazole-1-propanenitrile
77. alpha-(2-ethoxyphenyl)-alpha-(2-phenylethyl)-1H-1,2,4-triazole-1-propanenitrile
78. alpha-[2-(4-chlorophenyl)ethyl]-alpha-(2-ethoxyphenyl)-1H-1,2,4-triazole-1-propanenitrile
79. alpha-(2-ethoxyphenyl)-alpha-[2-(4-fluorophenyl)ethyl]-1H-1,2,4-triazole-1-propanenitrile
80. alpha-[2-(3,4-dichlorophenyl)ethyl]-alpha-phenyl-1H-1,2,4-triazole-1-propanenitrile
81. alpha-(3-chlorophenyl)-alpha-[2-(3-chlorophenyl)ethyl]-1H-1,2,4-triazole-1-propanenitrile
82. alpha-(3-chlorophenyl)-alpha-[2-(3-fluorophenyl)ethyl]-1H-1,2,4-triazole-1-propanenitrile
83. alpha-[2-(3-fluorophenyl)ethyl]-alpha-phenyl-1H-1,2,4-triazole-1-propanenitrile
84. alpha-[2-(3-chlorophenyl)ethyl]-alpha-(2-methoxyphenyl)-1H-1,2,4-triazole-1-propanenitrile
85. alpha-(4-bromophenyl)-alpha-[2-(3-chlorophenyl)ethyl]-1H-1,2,4-triazole-1-propanenitrile
86. alpha-(4-chlorophenyl)-alpha-[2-(3-fluorophenyl)ethyl]-1H-1,2,4-triazole-1-propanenitrile
87. alpha-(3-bromophenyl)-alpha-(2-phenylethyl)-1H-1,2,4-triazole-1-propanenitrile
88. alpha-[2-(3-bromophenyl)ethyl]-alpha-(2-ethoxyphenyl)-1H-1,2,4-triazole-1-propanenitrile
89. alpha-(3-fluorophenyl)-alpha-[2-(3-fluorophenyl)ethyl]-1H-1,2,4-triazole-1-propanenitrile
90. alpha-(4-bromophenyl)-alpha-[2-(3-bromophenyl)ethyl]-1H-1,2,4-triazole-1-propanenitrile
91. alpha-[2-(3-chlorophenyl)ethyl]-alpha-(3-fluorophenyl)-1H-1,2,4-triazole-1-propanenitrile
92. alpha-[2-(3,5-dichlorophenyl)ethyl]-alpha-phenyl-1H-1,2,4-triazole-1-propanenitrile
93. alpha-[2-(4-methoxyphenyl)ethyl]-alpha-phenyl-1H-1,2,4-triazole-1-propanenitrile
94. alpha-[2-(4-chlorophenyl)ethyl]-alpha-phenyl-beta-phenyl-1H-1,2,4-triazole-1-propanenitrile (one isomer at beta position)
95. alpha-[2-(4-chlorophenyl)ethyl]-alpha-(2-thienyl)-1H-1,2,4-triazole-1-propanenitrile
96. alpha-[2-(4-chlorophenyl)ethyl]-alpha-(2-pyridyl)-1H-1,2,4-triazole-1-propanenitrile.

The structures of the Compounds 1-96 are set forth in Table 1 below.

TABLE 1

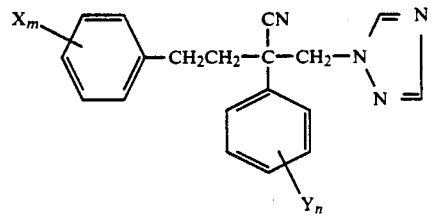

| Compound | $X_m$ | $Y_n$ |
|---|---|---|
| 1 | H | 4Cl |
| 2 | H | H |
| 3 | H | 2OCH$_3$ |
| 4 | H | 4F |
| 5 | H | 2,4Cl |
| 6 | 4Cl | 4Cl |
| 7 | 4F | 4Cl |
| 8 | 4CH$_3$ | 4Cl |
| 9 | 4OCH$_3$ | 4Cl |
| 10 | 4Cl | H |
| 11 | 4F | H |
| 12 | H | 4φ |
| 13 | 2CF$_3$ | H |
| 14 | 3CF$_3$ | H |
| 15 | 2,4Cl | H |
| 16 | 4Br | H |
| 17 | 2Cl | H |
| 18 | 3Cl | H |
| 19 | 4CF$_3$ | H |
| 20 | 3CF$_3$ | 4Cl |
| 21 | 3CF$_3$ | 4F |
| 22 | 4Br | 4Cl |
| 23 | 4CF$_3$ | 4Cl |
| 24 | 4CF$_3$ | 4F |
| 25 | 4Br | 4F |
| 26 | 4Cl | 4F |
| 27 | 3Br | H |
| 28 | 4F | 4F |
| 29 | 4CF$_3$ | 2OCH$_3$ |
| 30 | 3Cl | 4F |
| 31 | 3Cl | 4Cl |
| 32 | H | 4Br |
| 33 | 4F | 4Br |
| 34 | H | 3Cl |
| 35 | 4Cl | 3Cl |
| 36 | 4F | 3Cl |
| 37 | 4Cl | 4Br |
| 38 | 3Br | 4F |
| 39 | 3Br | 4Cl |
| 40 | 4Cl | 2Cl |
| 41 | 4Cl | 2F |
| 42 | 2F | 4Cl |
| 43 | 2F | 4F |
| 44 | 4F | 2Cl |
| 45 | 4F | 2F |
| 46 | 4Cl | 3CF$_3$ |
| 47 | 4Cl | 3F |
| 48 | 4Cl | 2Br |
| 49 | 4Cl | 2OCH$_3$ |
| 50 | H | 3CF$_3$ |
| 51 | 3CF$_3$ | 3CF$_3$ |
| 52 | H | 3F |
| 53 | 3CF$_3$ | 3Cl |
| 54 | H | 2Br |
| 55 | 3CF$_3$ | 2Br |
| 56 | 3CF$_3$ | 3F |

TABLE 1-continued

| | | |
|---|---|---|
| 57 | 3CF$_3$ | 2Cl |
| 58 | 2OCH$_3$ | H |
| 59 | 3OCH$_3$ | H |
| 60 | 3,4OCH$_3$ | H |
| 61 | 4Cl | 4OCH$_3$ |
| 62 | H | 4OCH$_3$ |
| 63 | H | 2Cl,6F |
| 64 | 4Cl | 2Cl,6F |
| 65 | 4Cl | 2,6Cl |
| 66 | 3Br | 3Cl |
| 67 | 4Br | 3Cl |
| 68 | 3Br | 3F |
| 69 | 4Br | 3F |
| 70 | See formula (III) below | |
| 71 | 4F | 3F |
| 72 | 4F | 3CF$_3$ |
| 73 | See formula (IV) below | |
| 74 | 4Br | 2OEt |
| 75 | 4Br | 3CF$_3$ |
| 76 | 3CF$_3$ | 2OEt |
| 77 | H | 2OEt |
| 78 | 4Cl | 2OEt |
| 79 | 4F | 2OEt |
| 80 | 3,4Cl | H |
| 81 | 3Cl | 3Cl |
| 82 | 3F | 3Cl |
| 83 | 3F | H |
| 84 | 3Cl | 2OCH$_3$ |
| 85 | 3Cl | 4Br |
| 86 | 3F | 4Cl |
| 87 | H | 3Br |
| 88 | 3Br | 2OEt |
| 89 | 3F | 3F |
| 90 | 3Br | 4Br |
| 91 | 3Cl | 3F |
| 92 | 3,5Cl | H |
| 93 | 4OCH$_3$ | H |
| 94 | See formula (V) below | |
| 95 | See formula (VI) below | |
| 96 | See formula (VII) below | |

70. 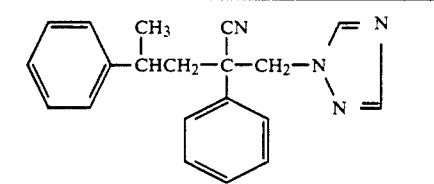   (III)

73. 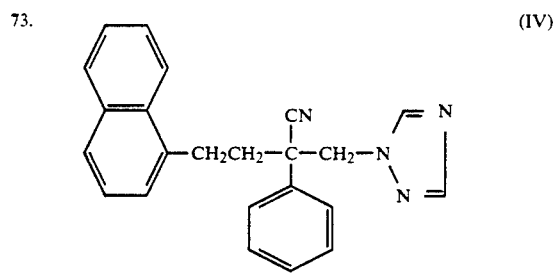   (IV)

94. 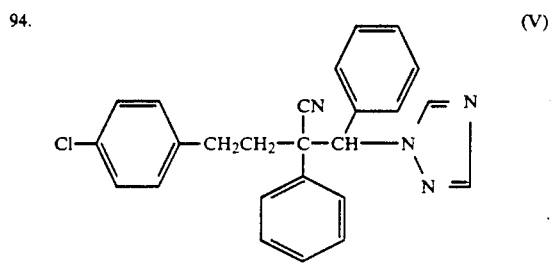   (V)

95. 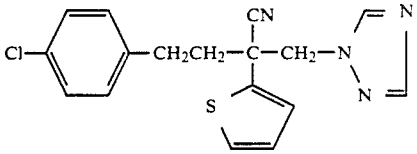   (VI)

96. 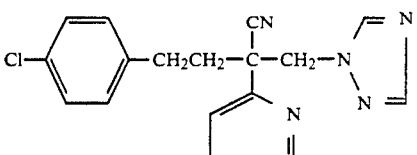   (VII)

Other examples which are included in the present invention are set forth in Table 2.

TABLE 2

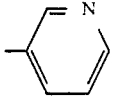

| Compound | Z | X$_m$ | Ar(Y$_n$) |
|---|---|---|---|
| 97 | —CH$_2$CH$_2$— | —H | -φ(4CH$_2$CH$_2$CH$_2$Cl) |
| 98 | —CH$_2$CH$_2$— | 4CH=CHF | -φ |
| 99 | —CH$_2$CH$_2$— | -φ(2,4Cl) | -φ |
| 100 | —CH$_2$CH$_2$— | 4CN | -φ(3CN) |
| 101 | —CH$_2$CH$_2$— | 4C(O)H | -φ |
| 102 | —CH$_2$CH$_2$— | 4NHCH$_3$ | -φ |
| 103 | —CH$_2$CH$_2$— | 2SCH$_3$ | -φ(4SO$_2$CH$_3$) |
| 104 | —CH=CH— | —H | -φ(3Cl) |
| 105 | —C≡C— | —H | -φ(4Cl) |
| 106 | —CH$_2$CH$_2$— | 4S(O)CH$_2$CH$_3$ | -φ |
| 107 | —CHClCH$_2$— | 4Cl | -ø |
| 108 | —CHClCHCl— | 4F | -φ |
| 109 | —CHBrCH$_2$— | 4Br | -φ |
| 110 | —CH$_2$CH$_2$— | 4Cl | 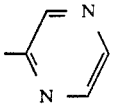 |
| 111 | —CH$_2$CH$_2$— | 4F | 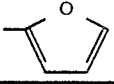 |
| 112 | —CH$_2$CH$_2$— | 4Br | (furan) |

Comparative compounds which were made and tested include:

C2a. alpha, alpha-diphenyl-1H-1,2,4-triazole-1-propanenitrile

C2b. alpha-benzyl-alpha-phenyl-1H-1,2,4-triazole-1-propanenitrile

C6. alpha-(4-chlorobenzyl)-alpha-(4-chlorophenyl)-1H-1,2,4-triazole-1-propanenitrile C10. alpha-(4-chlorobenzyl)-alpha-phenyl-1H-1,2,4-triazole-1-propanenitrile The structures of the Comparative compounds are set forth below.

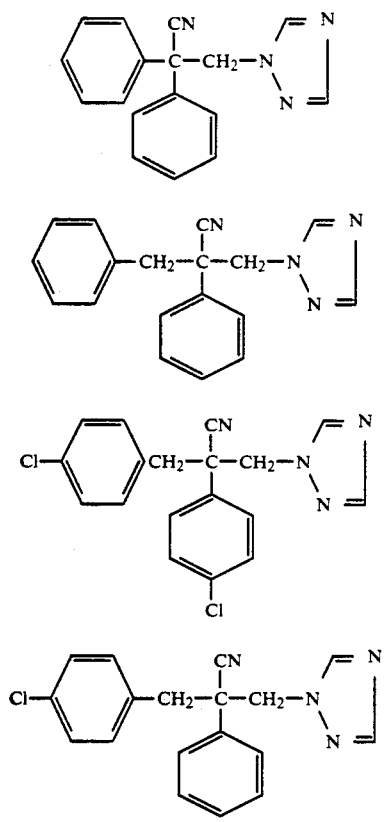

C2a.

C2b.

C6.

C10.

The triazoles of the present invention can be prepared by conventional synthesis routes. For example, the triazoles may be prepared by nucleophilic displacement of the alpha-(bromomethyl)-alpha-(2-phenylethyl)-phenylacetonitrile (VIII) by a salt, preferably an alkali metal salt, of the triazole, generally about 1 to about 3 equivalents. This reaction can be run either neat or, preferably, in an appropriate solvent such as dimethylsulfoxide (DMSO), N,N-dimethylformamide (DMF), toluene or xylene at a temperature from about 0° C. to about 150° C., preferably from about 25° C. to about 100° C. The compound VIII is prepared by bromomethylation of the alpha-2-phenylethyl-phenylacetonitrile (IX) by methylenebromide (generally about 1.1 to about 2 equivalents) under basic conditions, e.g., sodium or potassium hydroxide, sodium or potassium hydride, potassium methoxide and potassium-t-butoxide (generally about 1.1 to about 2 equivalents) preferably with the use of a solvent such as DMSO with sodium hydroxide or DMF with the hydrides and oxides, at a temperature from about 0° C. to about 150° C., preferably from about 25° C. to about 100° C. The compound IX can be prepared by phase transfer alkylation of the appropriately substituted benzylcyanides (X) with generally about 1 to about 2 equivalents of a 2-phenylethylmethanesulfonate (mesylate) or p-toluenesulfonate (tosylate) in the presence of a strong base, e.g., 50% (w/w) sodium hydroxide, and a catalyst, e.g., tetrabutylammonium bromide (TBABr). Compound IX can also be prepared by alkylation of the appropriately substituted benzylcyanide with about 1 to 2 equivalents of a 2-phenylethylhalide in the presence of a strong base such as metal hydrides, e.g. sodium or potassium hydride, using DMF or DMF/toluene as the solvent. Both the benzylcyanides and the alkyl halides can be readily prepared by techniques known from the literature. This synthesis scheme is shown below:

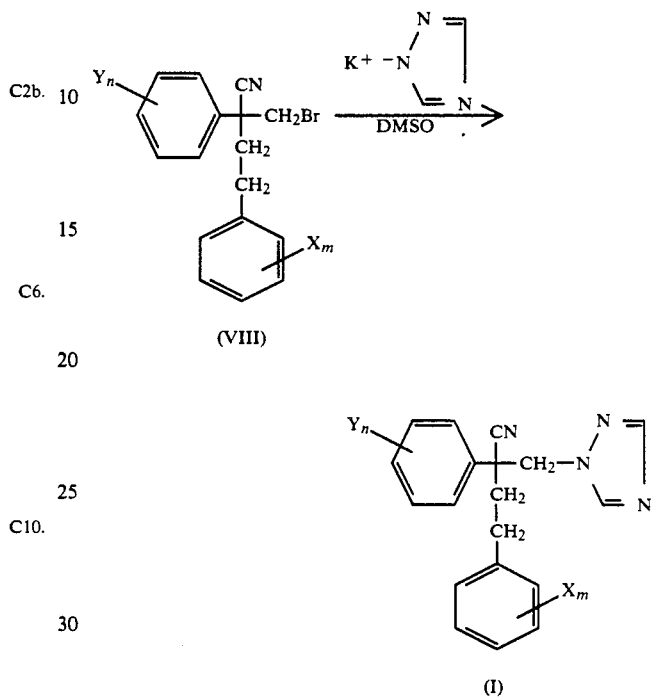

(VIII)

(I)

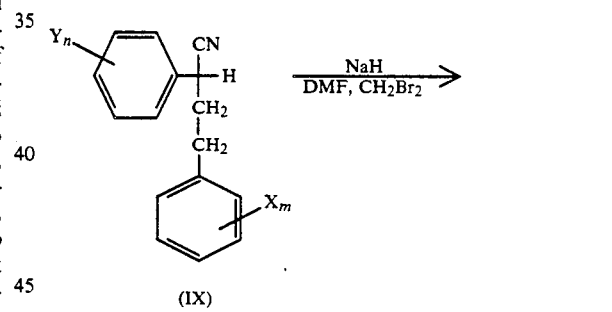

(IX)

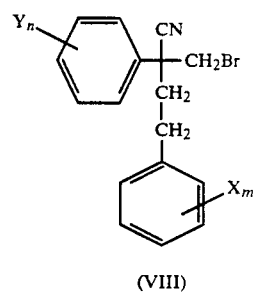

(VIII)

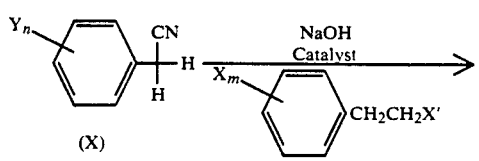

(X)

-continued

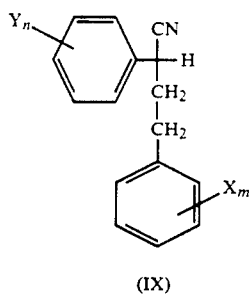

(IX)

The phenethyl triazole (I) can be prepared directly from the phenylethyl-phenylacetonitrile (IX) in one step by the reaction with a halomethyltriazole (XI) in a solvent such as DMF. Two equivalents of a strong base such as sodium hydride or potassium hydride are used. This synthesis scheme is shown below:

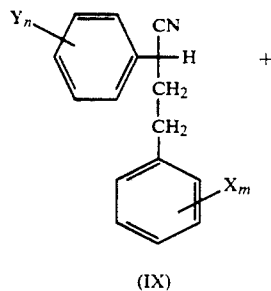

(IX)

$$\text{Hal}-CH_2-N\underset{N}{\overset{N}{\diagdown}}\xrightarrow[\text{DMF}]{\text{NaH}}$$

(XI)

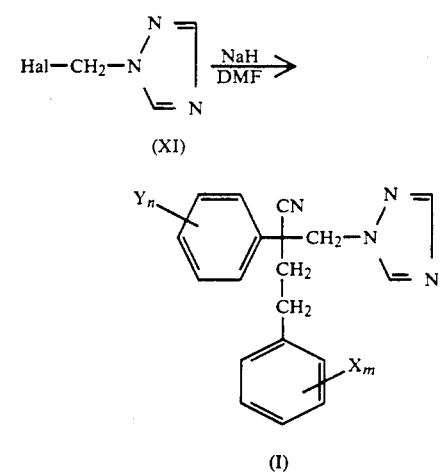

(I)

This reaction is not limited to the preparation of the triazoles of the present invention. The reaction can also be used to prepare compounds having a quaternary carbon bonded to an aryl group, a cyano group and a triazole group such as disclosed in U.S. Pat. No. 4,366,165 and British patent application 2,119,374. The method disclosed in the prior art requires the additional step of preparing an aryl-cyano-(halomethyl, alkylsulphonyloxymethyl or arylsulphonyloxymethyl) compound which is reacted with a triazole or an alkali metal triazole derivative. This extra step is eliminated by the process of the present invention.

The acid addition salts of the triazoles of this invention can be prepared by standard techniques well-known in the art. For example, the triazole of formula (I) can be dissolved in an appropriate solvent such as diethyl ether, tetrahydrofuran, ethanol, methanol and the like or combinations thereof and treated with an equivalent or excess amount of a mineral or organic acid which may or may not be dissolved in an appropriate solvent, the mixture is then either cooled or evaporated to give the salt which can either be used as such or recrystallized from an appropriate solvent or combination of appropriate solvents.

The metal salt complexes of the above triazoles of this invention can be prepared by adding dropwise, with stirring, a stoichiometric amount of a metal salt dissolved in an appropriate solvent or combination of solvents to a solution of the triazole of formula (I) dissolved in a similarly appropriate solvent or combination of solvents. The reaction mixture is briefly stirred and the solvent is removed under reduced pressure to give the metal salt complex of the respective triazoles of formula (II).

The metal salt complexes can also be prepared by mixing stoichiometric or excess amounts of the metal salt and a triazole of formula (I) in the desired amount of solvent containing the appropriate adjuvants just prior to spraying the plants. Adjuvants that may be included in this "in situ" preparation may be detergents, emulsifiers, wetting agents, spreading agents, dispersing agents, stickers, adhesives, and the like which are used in agricultural applications.

Solvents that can be utilized in these procedures include any polar solvent, e.g., water, methanol, ethanol, isopropanol or ethylene glycol and any aprotic dipolar solvent, e.g., dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Any appropriate anion, e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

The compounds of this invention possess an asymmetric carbon atom and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The enantiomorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a dispersing agent and a finely divided solid, such as clays, inorganic silicates and carbonates, and silicas, and optionally incorporating wetting agents and sticking agents in such mixtures. The concentration of active ingredients in such formulations is usually in the range of from about 20% to about 98%, preferably from about 40% to about 75%. A typical wettable powder is made by blending 50 parts of alpha-[2-(4-chlorophenyl)ethyl]-alpha-(2-methoxyphenyl)-1H-1,2,4-triazole-1-propanenitrile, 45 parts of a synthetic precipitated hydrated silicon dioxide sold under the trademark Hi-Sil ®, 1 part sodium lauryl sulfate and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium aluminate sold under the trademark Zeolex ® 7.

Dusts are prepared by mixing the triazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application can be readily determined by one in the art depending upon the type of equipment used, the desired method, timing and frequency of applications, plants to be treated and diseases to be controlled. Generally, however, the fungicidal compounds of the present invention will be applied in an amount of from about 0.01 to about 20 pounds of active ingredient per acre when applied foliarly or to the soil.

As a seed protectant, the amount of the compound coated on the seeds is usually from about 0.05 to about 4 ounces of active ingredient per hundred pounds of seed and preferably from 0.1 to about 1 ounce per hundred pounds of seed. As a soil fungicide the compounds can be incorporated in the soil or applied to its surface usually at a rate of from about 0.05 to about 20 pounds, preferably from about 0.02 to about 10 pounds and more preferably from about 0.1 to about 3 pounds of active ingredient per acre. As a foliar fungicide, the compounds are usually applied to growing plants at a rate of from about 0.01 to about 10 pounds, preferably from about 0.02 to about 5 and more preferably from about 0.03 to about 1 pound of active ingredient per acre.

Fungicides which can be combined with the fungicides of this invention include:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: Systhane (a registered trademark of Rohm and Haas for myclobutanil), triademifon, N-trichloro-methylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-1[bis(dimethylamino)-phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox) methyl 1-(butylcarbamoyl)-2-benzimidazole carbamate(benomyl),2-(4'-thiazolyl)-benzimidazole(thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin,alpha-(phenyl)-alpha-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl)-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate, and Bordeaux mixture;

(g) other rice fungicides such as: tricylazole, iso-prothiolane, probenazole, propiconazole, edifenphos, O-O-diisopropyl-benzyl-thiophosphate, iprodione, procymidone, vinclozolin, benomyl, thiophanate methyl, mepronil, tencycuron and validamycin A; and (h) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido)benzene(thiophanatemethyl).

The enantiomorphs, acid addition salts and metal salt complexes of this invention can be advantageously employed in various ways. Since these compounds possess broad spectrum fungicidal activity, they can be employed as fungicides in turf, fruit orchards, vegetable crops, cereal crops, golf course applications and the storage of cereal grain. Other applications of this invention will suggest themselves to those skilled in the art of agriculture and horticulture.

EXAMPLES

In summary, the substituted benzylcyanide was synthesized to the alpha-phenyl-alpha-(2-phenylethyl)-1H-1,2,4-triazole-1-propanenitrile in three steps. The benzylcyanide was alkylated in the first step by one of six methods. The alkylated phenylacetonitrile was bromomethylated in the second step by one of four methods. The alkylated triazole propanenitrile was synthesized from the alkylated phenylacetonitrile bromide by nucleophilic displacement with potassium triazole in the third step. In the third step the potassium triazole was either previously prepared and added to the bromide or equal parts of potassium hydroxide, triazole and DMSO was added to an equivalent amount of toluene, heated to 100°-120° C. for 2 hours to distill off the toluene and drive off the azeotropic water and the bromide added to the freshly prepared potassium triazole. In a third method the potassium triazole was prepared in situ by the reaction of potassium carbonate and triazole in a MEK or DMSO solvent.

A two step procedure can be used to prepare the alpha-phenyl-alpha-(2-phenylethyl)-1H-1,2,4-triazole-1-propanenitrile. The first step is the same as for the three step procedure. However the product of step 1 is coupled via a base with chloromethyltriazole.HCl in DMF. At least two equivalents of base is employed. The anion is generated at room temperature then the solid HCl salt is added. The second equivalent liberates the salt to the free base, chloromethyl triazole, which reacts with the anion. The base can be hydroxide, alkoxide or hydride. NaOH or KOH can be employed however NaH is preferred on an experimental scale. For less acidic intermediates where the anion is more difficult to form KH is preferred.

A similar procedure using chloromethyl triazole.HCl is to liberate the salt to the free base prior to addition. This can be done with NaOH in $CH_2Cl_2$, then the solvent removed and the addition done with DMF using NaH as the base or DMSO with NaOH as the base.

The halogenated phenethyl triazoles may be prepared from the corresponding phenethyl triazoles by the reaction with N-chlorosuccinimide (NCS) or N-bromosuccinimide (NBS) in the presence of a catalyst or initiator such as benzoyl peroxide. The phenethyl triazole is dissolved in an inert solvent such as carbon tetrachloride and 1 or 2 equivalents of the halogenating agent is used.

The halogenated triazoles can be transformed into the ethenyl compound by base elimination using a metal hydroxide or alkoxide. Typical bases include sodium hydroxide, sodium methoxide and potassium tert-butoxide.

A summary of the steps and the process of preparation of the Compounds 1–96 are set forth in Tables 3 and 4.

TABLE 3

| Step 1 | Step 2 | Step 3 |
|---|---|---|
| 1. 50% NaOH in DMSO or DMSO/toluene (50% NaOH) | 1. 50% NaOH in DMSO (50% NaOH) | 1. KTriazole previously prepared (KTr) |
| 2. 60% NaH in DMF (NaH/DMF) | 2. 60% NaH in DMF (NaH/DMF) | 2. KOHTriazole (KOHTr) |
| 3. 60% NaH in DMF, toluene (NaH/DMFT = 1:2 DMF:toluene, NaH/DMFt = 2:1 DMF:toluene) | 3. 60% NaH/35% KH in DMF (NaH/KH) | 3. $K_2CO_3$/Triazole ($K_2CO_3$/Tr) |
| 4. 60% NaH in DMF, benzene (NaH/DMFB) | 4. 35% KH in DMF (KH/DMF) | |
| 5. 60% NaH/100% KH in DMF (NaH,KH/DMF) | Step 2–3 ClCH₂Triazole (ClCH₂Tr) | |
| 6. 60% NaH/35% KH in DMF, toluene (NaH,KH/DMFT) | | |

TABLE 4

| Compound | Step 1 | Step 2 | Step 3 | m.p. °C. |
|---|---|---|---|---|
| 1 | 50% NaOH | 50% NaOH | KTr | 113–114 |
| 2 | NaH/DMF | NaH/DMF | KTr | 118–119 |
| 3 | NaH/DMF | 50% NaOH | KTr | 105–106 |
| 4 | NaH/DMF | 50% NaOH | KTr | 100–102 |
| 5 | NaH/DMF | NaH/THF | KTr | 128–129 |
| 6 | NaH/DMFt | 50% NaOH | KOHTr | 139–140 |
| 7 | NaH/DMF | NaH/DMF | KTr | 144–146 |
| 8 | NaH/DMF | NaH/DMF | KTr | 147–148 |
| 9 | NaH/DMF | NaH/DMF | KTr | 124–126 |
| 10 | NaH/DMF | 50% NaOH | KTr | 122–124 |
| 11 | NaH/DMF | 50% NaOH | KTr | 108–111 |
| 12 | NaH/DMFt | 50% NaOH | KTr | 168–169 |
| 13 | NaH/DMFt | 50% NaOH | KTr | 130–131 |

TABLE 4-continued

| Compound | Step 1 | Step 2 | Step 3 | m.p. °C. |
|---|---|---|---|---|
| 14 | NaH/DMFt | 50% NaOH | KOHTr | 127-128 |
| 15 | NaH/DMFt | 50% NaOH | KOHTr | 154-155 |
| 16 | NaH/DMF | 50% NaOH | KTr | 115-117 |
| 17 | NaH/DMFt | 50% NaOH | KOHTr | 113-114 |
| 18 | NaH/DMFt | 50% NaOH | KOHTr | 99-102 |
| 19 | NaH/DMFt | NaH/DMF | KOHTr | 133-134 |
| 20 | NaH/DMFB | 50% NaOH | KTr | 118-121 |
| 21 | NaH/DMFB | 50% NaOH | KTr | 85-88 |
| 22 | NaH/DMF | 50% NaOH | KTr | 142-143 |
| 23 | NaH/DMFT | 50% NaOH | KTr | 116-119 |
| 24 | NaH/DMFT | 50% NaOH | KTr | 119-121 |
| 25 | NaH/DMF | 50% NaOH | KTr | 135-137 |
| 26 | NaH/DMF | NaH/DMF | KTr | 121-122 |
| 27 | NaH/DMFT | 50% NaOH | KTr | 107-108 |
| 28 | NaH/DMF | 50% NaOH | KTr | Oil |
| 29 | NaH/DMFT | 50% NaOH | KTr | Oil |
| 30 | NaH/DMF | 50% NaOH | KOHTr | 113-114 |
| 31 | NaH/DMF | 50% NaOH | KOHTr | 88-90 |
| 32 | NaH/DMF | NaH/DMF | KTr | 119-120 |
| 33 | NaH/DMF | NaH/DMF | KTr | 145-146 |
| 34 | NaH/DMF | NaH/DMF | KTr | 95-97 |
| 35 | NaH/DMF | NaH/DMF | KTr | 119-120 |
| 36 | NaH/DMF | NaH/DMF | KTr | 119-120 |
| 37 | NaH/DMF | NaH/DMF | KTr | 136-137 |
| 38 | NaH/DMFT | 50% NaOH | K$_2$CO$_3$/Tr | 110-113 |
| 39 | NaH/DMFT | 50% NaOH | K$_2$CO$_3$/Tr | Oil |
| 40 | NaH/DMF | ClCH$_2$Tr | | 102-103 |
| 41 | NaH/DMF | ClCH$_2$Tr | | Oil |
| 42 | NaH/DMF | ClCH$_2$Tr | | 122-124 |
| 43 | NaH/DMF | ClCH$_2$Tr | | 102-103 |
| 44 | NaH/DMF | ClCH$_2$Tr | | 110-112 |
| 45 | NaH/DMF | ClCH$_2$Tr | | Oil |
| 46 | NaH/DMF | ClCH$_2$Tr | | 79-80 |
| 47 | NaH/DMF | ClCH$_2$Tr | | 115-117 |
| 48 | NaH/DMF | ClCH$_2$Tr | | 121-122 |
| 49 | NaH/DMF | ClCH$_2$Tr | | 134-135 |
| 50 | NaH/DMF | ClCH$_2$Tr | | Glass |
| 51 | NaH/DMF | ClCH$_2$Tr | | 80-81 |
| 52 | NaH/DMF | ClCH$_2$Tr | | 112-113 |
| 53 | NaH/DMF | ClCH$_2$Tr | | 72-73 |
| 54 | NaH/DMF | ClCH$_2$Tr | | 118-119 |
| 55 | NaH/DMF | ClCH$_2$Tr | | 96-97 |
| 56 | NaH/DMF | ClCH$_2$Tr | | 109-110 |
| 57 | NaH/DMF | ClCH$_2$Tr | | 93-94 |
| 58 | NaH/DMF | ClCH$_2$Tr | | Oil |
| 59 | NaH/DMFT | ClCH$_2$Tr | | 86-87 |
| 60 | NaH/DMFT | ClCH$_2$Tr | | Oil |
| 61 | NaH/DMF | NaH/DMF | KTr | 111-113 |
| 62 | NaH/DMF | NaH/DMF | KTr | 95-97 |
| 63 | NaH/DMFT | NaH/DMF | KTr | Oil |
| 64 | NaH/DMFT | NaH/DMF | KTr | 98-99 |
| 65 | NaH/DMFT | NaH/DMF | KTr | 108-109 |
| 66 | NaH/DMFT | NaH/DMF | KTr | 108-109 |
| 67 | NaH/DMFT | NaH/DMF | KTr | 112-113 |
| 68 | NaH/DMFT | NaH/DMF | KTr | 112-114 |
| 69 | NaH/DMFT | NaH/DMF | KTr | 115-117 |
| 70 | NaH/DMFT | ClCH$_2$Tr | | Oil |
| 71 | NaH/DMFT | NaH/DMF | KTr | 115-116 |
| 72 | NaH/DMFT | NaH/DMF | KTr | 82-83 |
| 73 | NaH/DMFT | NaH/DMF | KTr | 108-110 |
| 74 | NaH,KH/DMFT | KH/DMF | KTr | 130-132 |
| 75 | NaH/DMFT | NaH/DMF | KTr | Oil |
| 76 | NaH/DMF | KH/DMF | KTr | 96-98 |
| 77 | NaH/DMF | NaH/KH | KTr | 80 |
| 78 | NaH/DMF | NaH/KH | KTr | 126-128 |
| 79 | NaH/DMF | NaH/KH | KTr | 97-98 |
| 80 | NaH/DMFT | NaH/DMF | KTr | 144-146 |
| 81 | NaH/DMFT | NaH/DMF | KTr | 104-106 |
| 82 | NaH/DMFT | NaH/DMF | KTr | 98-100 |
| 83 | NaH/DMFT | ClCH$_2$Tr | | 100-101 |
| 84 | NaH/DMFT | ClCH$_2$Tr | | 103-104 |
| 85 | NaH/DMFT | ClCH$_2$Tr | | 96-98 |
| 86 | NaH/DMFT | ClCH$_2$Tr | | 126-128 |
| 87 | NaH/DMFT | ClCH$_2$Tr | | Oil |
| 88 | NaH,KH/DMF | ClCH$_2$Tr | | Oil |
| 89 | NaH/DMFT | ClCH$_2$Tr | | 115-117 |
| 90 | NaH/DMFT | ClCH$_2$Tr | | Oil |
| 91 | NaH/DMFT | ClCH$_2$Tr | | 108-110 |
| 92 | NaH/DMFT | ClCH$_2$Tr | | 130-131 |
| 93 | 50% NaOH | 50% NaOH | K$_2$CO$_3$/Tr | 91-94 |
| 94 | 50% NaOH | NaH/DMF | KTr | 244-248 |
| 95 | NaH/DMFT | NaH/DMF | KTr | Oil |
| 96 | NaH/DMF | ClCH$_2$Tr | | Oil |

The melting points and elemental analysis for Compounds 1-96 are set forth in Tables 4 and 5. The amount of chlorine, fluorine and oxygen were not measured in all of the examples. The NMR for Compounds 70, 95 and 96 follow Table 5.

TABLE 5

| Compound | Carbon Calc. | Carbon Found | Hydrogen Calc. | Hydrogen Found | Nitrogen Calc. | Nitrogen Found | Oxygen Calc. | Oxygen Found | Chlorine Calc. | Chlorine Found | Bromine Calc. | Bromine Found | Fluorine Calc. | Fluorine Found |
|---|---|---|---|---|---|---|---|---|---|---|---|---|---|---|
| 1 | 67.75 | 67.73 | 5.09 | 5.06 | 16.64 | 16.49 | | | 10.52 | 10.47 | | | | |
| 2 | 75.47 | 75.97 | 6.00 | 6.05 | 18.53 | 18.34 | | | | | | | | |
| 3 | 72.27 | 72.54 | 6.06 | 6.24 | 16.86 | 16.25 | 4.81 | 5.66 | | | | | | |
| 4 | 71.23 | 71.51 | 5.35 | 5.35 | 17.49 | 16.83 | | | | | | | 5.93 | 5.87 |
| 5 | 61.44 | 62.04 | 4.34 | 4.49 | 15.07 | 14.98 | | | 19.10 | 18.91 | | | | |
| 6 | 61.45 | 62.06 | 4.34 | 4.32 | 15.89 | 13.52 | | | 19.11 | 19.79 | | | | |
| 7 | 64.29 | 63.94 | 4.54 | 4.77 | 15.58 | 15.79 | | | 9.98 | 9.86 | | | 5.31 | 5.52 |
| 8 | 68.47 | 68.29 | 5.46 | 5.58 | 15.97 | 16.34 | | | 10.10 | 10.04 | | | | |
| 9 | 65.49 | 65.49 | 5.23 | 5.42 | 15.30 | 15.29 | 4.40 | 4.49 | 9.70 | 9.98 | | | | |
| 10 | 67.73 | 68.37 | 5.09 | 5.17 | 16.64 | 16.29 | | | 10.53 | 10.15 | | | | |
| 11 | 71.21 | 72.00 | 5.35 | 5.36 | 17.50 | 17.14 | | | | | | | 5.93 | 5.54 |
| 12 | 79.32 | 78.15 | 5.86 | 5.69 | 14.81 | 14.09 | | | | | | | | |
| 13 | 64.83 | 64.35 | 4.63 | 4.62 | 15.14 | 14.86 | | | | | | | 15.39 | 15.58 |
| 14 | 64.83 | 65.13 | 4.63 | 4.53 | 15.14 | 15.09 | | | | | | | 15.39 | 15.22 |
| 15 | 61.44 | 61.30 | 4.34 | 4.38 | 15.10 | 14.86 | | | 19.11 | 19.00 | | | | |
| 16 | 59.83 | 61.68 | 4.49 | 4.67 | 14.70 | 14.28 | | | | | 20.96 | 19.10 | | |
| 17 | 67.73 | 67.71 | 5.09 | 5.00 | 16.64 | 16.41 | | | 10.53 | 10.98 | | | | |
| 18 | 67.73 | 67.69 | 5.09 | 5.21 | 16.64 | 16.41 | | | 10.53 | 10.79 | | | | |
| 19 | 64.63 | 64.64 | 4.63 | 4.84 | 15.74 | 14.89 | | | | | | | 15.39 | 15.17 |
| 20 | 59.32 | 59.46 | 3.99 | 4.20 | 13.86 | 13.25 | | | 8.76 | 9.48 | | | 14.09 | 13.36 |
| 21 | 61.83 | 62.65 | 4.16 | 4.24 | 14.41 | 13.71 | | | | | | | 19.57 | 17.89 |
| 22 | 56.87 | 57.98 | 3.88 | 3.88 | 13.48 | 13.06 | | | 8.53 | 9.73 | 19.23 | 18.87 | | |
| 23 | 59.32 | 59.11 | 3.99 | 4.00 | 13.85 | 13.20 | | | 8.76 | 9.16 | | | 14.09 | 13.65 |
| 24 | 61.83 | 61.85 | 4.16 | 4.31 | 14.44 | 13.61 | | | | | | | 19.67 | 19.36 |
| 25 | 57.13 | 57.80 | 4.04 | 4.05 | 14.04 | 13.69 | | | | | 20.02 | 19.57 | 4.76 | 4.78 |
| 26 | 64.29 | 64.23 | 4.55 | 4.65 | 15.80 | 15.45 | | | 9.99 | 9.54 | | | 5.36 | 5.30 |
| 27 | 59.83 | 60.85 | 4.49 | 4.27 | 14.70 | 14.28 | | | | | 20.96 | 19.47 | | |
| 28 | 67.42 | 68.26 | 4.76 | 4.79 | 16.56 | 16.33 | | | | | | | 11.23 | 10.78 |

TABLE 5-continued

| Compound | Carbon Calc. | Carbon Found | Hydrogen Calc. | Hydrogen Found | Nitrogen Calc. | Nitrogen Found | Oxygen Calc. | Oxygen Found | Chlorine Calc. | Chlorine Found | Bromine Calc. | Bromine Found | Fluorine Calc. | Fluorine Found |
|---|---|---|---|---|---|---|---|---|---|---|---|---|---|---|
| 29 | 62.99 | 63.16 | 4.78 | 5.07 | 13.99 | 13.62 | 4.01 | | | | | | 14.23 | 14.37 |
| 30 | 64.29 | 64.35 | 4.55 | 4.54 | 15.80 | 15.74 | | | 9.99 | 10.09 | | | 5.86 | |
| 31 | 61.94 | 61.83 | 4.35 | 4.53 | 25.20 | 24.93 | | | 19.10 | 19.28 | | | | |
| 32 | 59.83 | 59.92 | 4.49 | 4.64 | 14.70 | 14.16 | | | | | | | 20.96 | 21.43 |
| 33 | 57.13 | 57.32 | 4.04 | 4.34 | 14.04 | 13.66 | | | | | 20.02 | 20.16 | 4.78 | 4.60 |
| 34 | 67.13 | 66.66 | 5.09 | 5.07 | 16.64 | 16.02 | | | 10.53 | 10.56 | | | | |
| 35 | 61.44 | 61.42 | 4.34 | 4.47 | 15.10 | 14.75 | | | 19.11 | 19.05 | | | | |
| 36 | 63.75 | 63.85 | 5.35 | 4.73 | 15.66 | 15.32 | | | 9.91 | 9.90 | | | 5.31 | 4.83 |
| 37 | 54.87 | 55.20 | 3.88 | 4.08 | 13.48 | 12.44 | | | 8.53 | 7.70 | 19.23 | 20.31 | | |
| 38 | 57.13 | 57.37 | 4.04 | 4.25 | 14.04 | 14.25 | | | | | 20.02 | 20.05 | 4.76 | |
| 39 | 54.87 | 54.40 | 3.88 | 4.48 | 13.48 | 11.88 | | | 8.53 | 8.60 | 19.23 | 17.77 | | |
| 40 | 61.44 | 61.19 | 4.35 | 4.32 | 15.10 | 14.95 | | | 19.10 | 18.88 | | | | |
| 41 | 64.29 | 61.57 | 4.55 | 4.58 | 15.80 | 14.88 | | | 10.00 | 10.44 | | | 5.36 | 4.86 |
| 42 | 64.29 | 63.73 | 4.55 | 4.53 | 15.79 | 15.46 | | | 10.00 | 9.89 | | | 5.35 | 5.37 |
| 43 | 67.42 | 67.14 | 4.77 | 4.82 | 16.56 | 16.46 | | | | | | | 11.24 | 11.16 |
| 44 | 64.30 | 63.82 | 4.55 | 4.56 | 15.89 | 15.84 | | | 10.00 | 9.87 | | | 5.36 | 5.30 |
| 45 | 66.52 | 67.42 | 4.77 | 5.00 | 16.57 | 16.56 | | | | | | | 11.24 | 11.39 |
| 46 | 59.31 | 59.58 | 3.99 | 4.08 | 13.84 | 13.65 | | | 8.76 | 8.58 | | | 14.09 | 14.02 |
| 47 | 64.29 | 64.12 | 4.55 | 4.52 | 15.80 | 15.27 | | | 9.99 | 10.19 | | | 5.36 | 4.97 |
| 48 | 54.87 | 54.80 | 3.88 | 4.24 | 13.48 | 13.30 | | | 8.53 | 8.50 | 19.23 | 19.17 | | |
| 49 | 65.46 | 65.54 | 5.22 | 5.23 | 15.28 | 14.61 | 4.36 | 5.14 | 9.67 | 9.44 | | | | |
| 50 | 64.83 | 65.02 | 4.63 | 4.62 | 15.14 | 15.13 | | | | | | | 15.40 | 15.58 |
| 51 | 57.52 | 57.53 | 3.68 | 3.74 | 12.79 | 12.77 | | | | | | | 26.02 | 25.85 |
| 52 | 71.21 | 70.96 | 5.35 | 5.47 | 17.50 | 17.51 | | | | | | | 5.93 | 5.82 |
| 53 | 59.31 | 59.65 | 4.15 | 4.26 | 14.43 | 13.94 | | | 8.76 | | | | 14.09 | 13.87 |
| 54 | 59.83 | 59.92 | 4.49 | 4.61 | 14.70 | 14.68 | | | | | 20.97 | 20.77 | | |
| 55 | 53.45 | 53.05 | 3.59 | 3.54 | 12.48 | 12.29 | | | | | 17.79 | 17.68 | 12.70 | 12.59 |
| 56 | 61.83 | 61.92 | 4.15 | 4.26 | 14.43 | 14.48 | | | | | | | 19.58 | 19.47 |
| 57 | 59.31 | 59.68 | 3.99 | 4.17 | 13.84 | 13.76 | | | 8.76 | 8.80 | | | 14.08 | 13.86 |
| 58 | 72.25 | 72.21 | 6.07 | 6.61 | 16.87 | 15.66 | 4.82 | 6.20 | | | | | | |
| 59 | 72.25 | 72.53 | 6.07 | 5.89 | 16.87 | 15.79 | 4.82 | 5.43 | | | | | | |
| 60 | 69.57 | 68.93 | 6.12 | 6.43 | 15.47 | 15.03 | 8.83 | 9.85 | | | | | | |
| 61 | 65.46 | 65.87 | 5.22 | 5.34 | 15.28 | 14.82 | 4.36 | 4.68 | 9.67 | 9.59 | | | | |
| 62 | 72.25 | 72.25 | 6.07 | 6.21 | 16.96 | 16.62 | 4.81 | 5.09 | | | | | | |
| 63 | 64.30 | 64.73 | 4.55 | 4.86 | 15.80 | 14.66 | | | 9.99 | 9.93 | | | 5.36 | 4.80 |
| 64 | 58.60 | 58.43 | 3.89 | 3.91 | 14.40 | 14.43 | | | 18.22 | 17.89 | | | 4.88 | 4.78 |
| 65 | 56.22 | 56.49 | 3.73 | 3.79 | 13.82 | 13.79 | | | 26.23 | 26.17 | | | | |
| 66 | 54.87 | 54.87 | 3.88 | 3.90 | 13.48 | 13.56 | | | 8.53 | 8.52 | 19.23 | 18.77 | | |
| 67 | 54.87 | 54.79 | 3.88 | 3.90 | 13.48 | 13.47 | | | 8.53 | 8.85 | 19.23 | 18.83 | | |
| 68 | 57.13 | 57.03 | 4.04 | 4.09 | 14.04 | 14.14 | | | | | 20.02 | 19.46 | 4.76 | 4.94 |
| 69 | 57.13 | 57.04 | 4.04 | 4.08 | 14.04 | 14.04 | | | | | 20.02 | 19.48 | 4.76 | 4.81 |
| 70 | See NMR | | | | | | | | | | | | | |
| 71 | 67.42 | 65.20 | 4.77 | 5.01 | 16.59 | 14.56 | | | | | | | 11.24 | 11.09 |
| 72 | 61.83 | 61.92 | 4.16 | 4.15 | 14.43 | 14.36 | | | | | | | 19.58 | 19.81 |
| 73 | 78.36 | 78.49 | 5.72 | 5.74 | 15.91 | 15.81 | | | | | | | | |
| 74 | 59.28 | 59.42 | 4.98 | 5.06 | 13.18 | 13.12 | 3.76 | 3.99 | | | 18.80 | 18.60 | | |
| 75 | 53.45 | 53.21 | 3.59 | 3.78 | 12.48 | 12.46 | | | | | 17.79 | 17.14 | 12.69 | 12.03 |
| 76 | 63.74 | 62.62 | 5.11 | 5.28 | 13.76 | 13.41 | 3.86 | | | | | | 13.76 | 13.68 |
| 77 | 72.79 | 73.19 | 6.41 | 6.40 | 16.18 | 16.12 | 4.62 | 4.80 | | | | | | |
| 78 | 66.09 | 66.31 | 5.26 | 5.37 | 13.76 | 13.73 | 4.64 | 4.21 | 10.00 | 9.92 | | | | |
| 79 | 68.79 | 68.89 | 5.77 | 5.67 | 15.49 | 15.31 | 4.80 | 4.73 | | | | | 5.36 | 5.40 |
| 80 | 61.44 | 60.53 | 4.34 | 4.07 | 15.10 | 14.60 | | | 19.11 | 18.77 | | | | |
| 81 | 61.44 | 61.16 | 4.34 | 4.17 | 15.10 | 15.18 | | | 19.11 | 19.36 | | | | |
| 82 | 64.30 | 64.32 | 4.55 | 4.15 | 15.80 | 16.02 | | | 10.00 | 10.23 | | | 5.36 | 5.16 |
| 83 | 71.21 | 71.20 | 5.35 | 5.36 | 17.50 | 17.44 | | | | | | | 5.93 | 5.93 |
| 84 | 65.46 | 65.53 | 5.22 | 5.25 | 15.28 | 15.23 | 4.36 | 4.34 | 9.67 | 9.22 | | | | |
| 85 | 54.87 | 54.81 | 3.88 | 3.78 | 13.48 | 13.34 | | | 8.53 | 8.00 | 19.23 | 18.90 | | |
| 86 | 64.30 | 64.35 | 4.55 | 4.85 | 15.80 | 15.64 | | | 10.00 | 9.99 | | | 5.36 | 5.15 |
| 87 | 59.83 | 58.56 | 4.50 | 4.51 | 14.70 | 13.56 | | | | | 20.96 | 20.91 | | |
| 88 | 59.28 | 58.40 | 4.98 | 5.43 | 13.18 | 11.56 | 3.76 | | | | 18.80 | 17.69 | | |
| 89 | 67.43 | 67.87 | 4.77 | 4.89 | 16.59 | 16.46 | | | | | | | 11.24 | 11.54 |
| 90 | 49.57 | 49.69 | 3.51 | 3.31 | 12.18 | 11.97 | | | | | 34.74 | 34.61 | | |
| 91 | 64.31 | 64.10 | 4.51 | 4.62 | 15.80 | 15.52 | | | 10.01 | 9.96 | | | 5.36 | 5.31 |
| 92 | 61.45 | 61.54 | 4.31 | 4.52 | 15.09 | 15.06 | | | 19.14 | 19.08 | | | | |
| 93 | 72.24 | 72.55 | 6.06 | 6.39 | 16.87 | 16.09 | 4.82 | 5.21 | | | | | | |
| 94 | 72.73 | 72.03 | 5.09 | 5.12 | 13.58 | 12.31 | | | 8.61 | 8.72 | | | | |
| 95 | See NMR | | | | | | | | | | | | | |
| 96 | See NMR | | | | | | | | | | | | | |

NMR was measured for Compounds 70, 95 and 96. The results are as follows:

Compound 70: NMR(90 MHz): (Mixture of diastereoisomers): 1.2–1.6(two doublets, 3H), 2.4–2.8(m, 3H), 4.6–4.9(two overlapping ABq, 2H), 7.0–7.8(m, 10H), 7.90(s, 1H) and 8.0(s, 1H).

Compound 95: NMR(90 MHz): 2.0–2.4(m, 4H), 4.8(ABq, 2H), 6.9–7.4(m, 7H), 7.8(s, 1H) and 7.9(s, 1H).

Compound 96: NMR(90 MHz): 2.2–2.9(m, 4H), 4.7–5.0(ABq, 2H), 7.0–7.4(ABq, 4H), 7.4–7.8(m, 3H) and 8.6–8.7(br d, 1H).

The following are examples of the preparation of typical compounds of the present invention.

PREPARATION OF COMPOUND 14

Alpha-phenyl-alpha-[2-(3-trifluoromethylphenyl)ethyl]-1,2,4-triazole-1-propanenitrile Step 1—Preparation of alpha-[2-(3-trifluoromethylphenyl)ethyl]phenylacetonitrile A 500 ml 4 neck round bottom flask was charged with 11.0 gms of 60% NaH (0.275 mole, 1.1 eq.), washed twice with hexane, in 50 ml of dry DMF. The reaction was cooled to 0° C. and 29.4 gms of benzyl cyanide (0.25 mole, 1.0 eq.) in 50 ml of toluene was added dropwise. The reaction was warmed to room temperature and then cooled to −20° C. and 52 gms (0.25 mole, 1.0 eq.) of 3-trifluoromethylphenethyl chloride in 50 ml of DMF was added dropwise. The reaction was stirred at −20° C. for 3 hours after which gas liquid chromatography showed 60% monoalkylation and 40% dialkylation. The reaction was quenched with water and extracted with ether. After drying and concentrating, the crude product was chromatographed by high pressure liquid chromatography (95:5) hexane:ethyl acetate and gave 19.2 gms of 97% pure product (26.3% yield). The mixture was added directly in the next step.

NMR (60 MHz): 2.0–2.4(m, 2H), 2.7–3.0(m, 2H), 3.6–3.9(t, 1H) and 7.2–7.4(d, 9H).

Step 2—Preparation of 1-bromo-2-cyano-2-phenyl-4-(3-trifluoromethylphenyl)butane A 500 ml 4 neck flask was charged with 19.0 gms of alpha-[2-(3-trifluoromethylphenyl)ethyl]phenyl acetonitrile (0.064 mole, 1.0 eq.) and 17 gms of $CH_2Br_2$ (0.097 mole, 1.5 eq.) in 50 ml of DMSO. The reaction was stirred at room temperature and 10.3 gms of 50% NaOH (0.128 mole, 2.0 eq.) was added dropwise. The reaction was warmed to 50° C. and stirred for 2 hours. The reaction was worked up with water and ether and gave after drying and concentrating 25 gms of product which was used directly in the triazole coupling (96.9% yield).

NMR (60 MHz): 2.2–2.8(m, 4H), 3.7(s, 2H) and 7.2–7.6(m, 9H).

Step 3—Preparation of alpha-phenyl-alpha-[2-(3-trifluoromethylphenyl)ethyl]-1,2,4-triazole-1-propanenitrile A 250 ml 4 neck round bottom flask was charged with 4.05 gms of 87% KOH (0.062 mole, 1.25 eq.) and 4.8 gms (0.068 mole, 2.2 eq.) of triazole in 25 ml DMSO. The reaction was warmed to 90° C. until homogeneous and 25 ml of toluene was added and azeotroped for 4 hours. The toluene was distilled off at 165° C. and the reaction was cooled to 100° C. and 12.5 g of 1-bromo-2-cyano-2-phenyl-4-(3-trifluoromethylphenyl)butane (0.031 mole, 1.0 eq.) was added. The reaction was heated at 125° C. for 1 hour and then worked up with water and ethyl acetate, dried and concentrated. Purification by high pressure liquid chromatography (1:1) hexane:ethyl acetate gave 8.8 gms of a white solid having a melting point of 127°–128° C. (76.7% yield).

IR (nujol, cm$^{-1}$): 2980(s), 2240(w), 1430(s), 1380(s) 1330(s), 1280(m) 1200(m), 1160(s), 1140(s), 1130(s), 1120(s), 1075(m), 1025(w), 800(m), 710(s) and 670(s).

NMR (60 MHz): 2.4–2.9(m, 4H), 4.6(s, 2H), 7.3–7.5(s, 4H), 7.7(s, 1H) and 7.9(s, 1H).

Elemental Analysis: $C_{20}H_{17}N_4F_3$: Theor: C: 64.83, H: 4.63, N:15.14, F: 15.39. Found: C: 65.13, H: 4.52, N: 15.09, F: 15.22.

PREPARATION OF COMPOUND 20

Alpha-(4-chlorophenyl)-alpha-[2-(3-trifluoromethylphenyl)ethyl]-1,2,4-triazole-1-propanenitrile Step 1—Preparation of alpha-[2-(3-trifluoromethylphenyl)ethyl]-4-chlorophenylacetonitrile A 1 neck 500 ml round bottom flask was charged with 4.4 gms of 60% NaH (0.11 mole, 1.0 eq.), washed three times with 25 ml hexanes, in 100 ml of 2:1 benzene/DMF. Then 15.1 gms (0.10 mole, 1.0 eq.) of 4-chlorobenzyl cyanide was added and stirred for 2 hours at room temperature. While stirring at room temperature 20.8 gms (0.1 mole, 1.0 eq.) of 3-(trifluoromethyl)-phenethyl chloride was added dropwise over several hours and then stirred at room temperature overnight. The product was worked up with water and ether and distilled after concentrating to give 16.2 gms of product (50.1% yield).

NMR (60 MHz): 2.0–3.0(m, 4H), 3.5–3.8(t, 1H), 7.3(s, 4H) and 7.5(s, 4H).

Step 2—Preparation of 1-bromo-2-cyano-2-(4-chlorophenyl)-4-(3-trifluoromethylphenyl)butane A 1 neck 300 ml round bottom flask was charged with 16.2 gms (0.05 mole, 1.0 eq.) of alpha-[2-(3-trifluoromethylphenyl)ethyl]-4-chlorophenylacetonitrile and 17.4 gms of $CH_2Br_2$ (0.10 mole, 2.0 eq.) in 50 ml of DMSO. The reaction was stirred at room temperature and 10 gms of 50% NaOH was added dropwise and an exotherm was observed. The reaction was stirred for 45 minutes and gas liquid chromatography showed the reaction was complete. The product was worked up with ether and water. Drying and removal of the solvent gave 20.8 gms of a yellow oil (100% yield).

NMR (60 MHz): 2.0–3.2(m, 4H), 3.8(s, 2H) and 7.5–7.6(d, 10H).

Step 3—Preparation of alpha-(4-chlorophenyl)-alpha-[2-(3-trifluoromethylphenyl)ethyl]-1,2,4-triazole-1-propanenitrile A 500 ml 1 neck round bottom flask was charged with 10.7 gms of potassium triazole (0.10 mole, 4.0 eq.), 75 ml of DMSO and 1-bromo-2-cyano-2-(4-chlorophenyl)-4-(3-trifluoromethylphenyl)butane (10.4 gms, 0.025 mole, 1.0 eq.). The reaction was heated at 80° C. overnight and then quenched by adding 1 liter of $H_2O$ and extracted three times with 200 ml of ether. The combined ether extracts were washed with water and brine, then dried and rotovaped to give a crude product which was slurried in ether:hexane (1:1). A solid formed which was washed with hexane and gave 5.0 gms of a light yellow solid having a melting point of 118°–121° C. (47% yield).

NMR (60 MHz): 2.4–3.2(m, 4H), 5.0–5.2(br s, 2H), 7.6–7.9(br s, 8H), 8.1(s, 1H) and 8.4(s, 1H).

Elemental Analysis: $C_{20}H_{16}N_4F_3Cl$: Theor: C: 59.32, H: 3.99, N: 13.85, Cl: 8.76, F: 14.09. Found: C: 59.46, H: 4.20, N: 13.25, Cl: 9.48, F: 13.36.

PREPARATION OF COMPOUND 44

Alpha-(2-chlorophenyl)-alpha-[2-(4-fluorophenyl)ethyl]-1,2,4-triazole-1-propanenitrile Step 1—Preparation of 2-(4-fluorophenyl)ethyl methanesulfonate; mesylation of 2-(4-fluorophenyl)ethanol A 500 ml 3 neck round bottom flask stirred under nitrogen equipped with condenser and addition funnel was charged with 42.04 gms of 2-(4-fluorophenyl)ethanol (0.3 mole, 1.0 eq.) in 100 ml of tetrahydrofuran (THF). The reaction was cooled to 10° C. and 60.7 gms (0.60 mole, 2.0 eq.) of triethylamine was added directly. This was followed by dropwise addition of 68.73 grams (0.6 mole, 2.0 eq.) of methanesulfonyl chloride in 30 ml of THF maintaining the temperature below 30° C. An additional 150 ml of THF was added and the reaction stirred for 6 hours. The reaction was quenched with 200 ml of water and 300 ml of ether was added. The ether was washed with 75 ml of 10% HCl, twice with 50 ml of saturated NaHCO$_3$, twice with 50 ml of water, dried and concentrated to give 58.0 gms of a brown liquid (88.7% yield).

NMR (90 MHz): 2.9(s, 3H), 2.9–3.2(m, 2H), 4.2–4.4(t, 2H) and 6.9–7.4(m, 4H).

Step 2—Preparation of alpha-[2-(4-fluorophenyl)ethyl]-2-chlorophenylacetonitrile A 4 neck 300 ml round bottom flask was charged with 4.26 gms of 60% NaH (0.105 mole, 1.05 eq.), washed three times with 25 ml of hexanes, in 60 ml of DMF. Then 15.16 gms (0.10 mole, 1.0 eq.) of 2-chlorophenyl acetonitrile in 40 ml of DMF was added and stirred for 1 hour at 10° C. Then 2-(4-fluorophenyl)ethyl methanesulfonate (22.2 gms, 0.102 mole) in 50 ml of DMF was added dropwise. The reaction was complete after 2 hours, then quenched with 10 ml of 10% HCl. Then 60 ml of water was added and extracted with 200 ml of ether which was then washed twice with 50 ml of 10% HCl, then dried and concentrated. 27.15 gms of crude product resulted which was distilled under reduced pressure and gave 17.46 gms of an oil having a boiling point of 180°–188° C. at 1 mm of Hg (63.5% yield).

NMR (90 MHz): 2.2–2.4(t, 2H), 2.8–3.0(m, 2H), 3.8–3.9(t, 2H) and 6.9–7.5(m, 8H).

Step 3—Preparation of alpha-(2-chlorophenyl)-alpha-[2-(4-fluorophenyl)ethyl]-1,2,4-triazole-1-propanenitrile A 200 ml 3 neck round bottom flask was charged with 2.3 gms of 60% NaH (0.055 mole, 2.75 eq.), washed twice with 25 ml hexanes, in 40 ml of DMF. The reaction was cooled to 10° C. and 5.46 gms (0.02 mole, 1.0 eq.) of alpha-[2-(4-fluorophenyl)ethyl]-2-chlorophenylacetonitrile in 40 ml of DMF was added dropwise over ten minutes. After 20 minutes, 3.12 gms (0.0204 mole, 1.02 eq.) of chloromethyltriazole.HCl was added directly in two portions. After 1 hour, gas liquid chromatography indicated the reaction was complete and the reaction was quenched by slowly adding 20 ml of water. The product was extracted with 200 ml of CH$_2$Cl$_2$ and washed twice with 50 ml of water. After drying and concentrating, an orange oil was obtained which crystallized from ethyl ether. The product was filtered and gave 2.5 gms of a light tan solid having a melting point of 110°–112° C. (35% yield).

IR (nujol, cm$^{-1}$): 1505(m), 1440(s), 1370(m), 1270(m), 1220(m), 1130(m) and 750(m).

NMR (90 MHz): 2.2–3.0(m, 4H), 3.8–4.2(ABq, 2H), 6.9–7.4(m, 7H), 7.8(s, 1H) and 7.9(s, 1H).

Elemental Analysis: C$_{19}$H$_{16}$N$_4$FCl: Theor: C: 64.30, H: 4.55, N: 15.80, F: 5.36, Cl: 10.00. Found: C: 63.82, H: 4.56, N: 15.84, F: 5.30, Cl: 9.87.

PREPARATION OF COMPOUND 64

Alpha-(2-chloro-6-fluorophenyl)-alpha-[2-(4-chlorophenyl)ethyl]-1,2,4-triazole-1-propanenitrile Step 1—Preparation of alpha-[2-(4-chlorophenyl)ethyl]-2-chloro-6-fluorophenylacetonitrile A 3 neck 200 ml round bottom flask was charged with 7.5 gms of 60% NaH (0.187 mole, 1.5 eq.), washed three times with 25 ml hexanes, in 60 ml of 2:1 toluene:DMF. To this was added 21.2 gms (0.125 mole, 1.0 eq.) of 2-chloro-6-fluorophenylacetonitrile dropwise over 0.5 hour in 40 ml of 2:1 toluene:DMF. The reaction was stirred for 20 minutes at 10° C. then at room temperature for 1 hour after which 32.1 gms of 2-(4-chlorophenyl)ethyl methanesulfonate (0.137 mole, 1.1 eq.) in 60 ml of 2:1 toluene:DMF was added dropwise over 1 hour. Approximately 70 ml of 2:1 toluene:DMF was added to permit constant stirring and the reaction was stirred for an additional 3.5 hours after which gas liquid chromatography indicated the reaction was complete. Then 50 ml of water was added, followed by 10 ml of 10% HCl and 300 ml of ether. The ether was washed with 100 ml of water which was extracted twice with 50 ml of ether then washed with water. The combined ethers were dried and concentrated to give 40.0 gms of crude product which was distilled under reduced pressure. 26.6 gms (69.8%) of product resulted having a boiling point of 175°–185° C. at 1 mm Hg.

NMR (90 MHz): 2.2–2.9(m, 4H), 4.2–4.4(t, 1H) and 7.0–7.4(m, 7H).

Step 2—Preparation of 1-bromo-2-cyano-2-(2-chloro-6-fluorophenyl)-4-(4-chlorophenyl)butane A 3 neck 200 ml round bottom flask was charged with 2.4 gms of 60% NaH (0.048 mole, 1.2 eq.), washed twice with 25 ml of hexanes, in 40 ml of DMF. At room temperature 12.28 gms (0.04 mole, 1.0 eq.) of alpha-[2-(4-chlorophenyl)ethyl]-2-chloro-6-fluorophenylacetonitrile was added dropwise over 0.5 hour in 30 ml of DMF. Then 10.43 gms of CH$_2$Br$_2$ (0.60 mole, 1.5 eq.) in 20 ml of DMF was added dropwise and the reaction was stirred at room temperature for 0.5 hour after which gas liquid chromatography indicated that the reaction was complete. The reaction was quenched after 1 hour by adding 20 ml of water and 200 ml of ether which was separated. After washing with water, drying and concentrating 14.84 gms (92.9% yield) resulted which was used directly in the triazole coupling.

NMR (90 MHz): 2.4–2.8(m, 4H), 3.8–4.2(ABq, 2H) and 6.9–7.3(m, 7H).

Step 3—Preparation of alpha-(2-chloro-6-fluorophenyl)-alpha-[2-(4-chlorophenyl)ethyl]-1,2,4-triazole-1-propanenitrile A 200 ml 1 neck round bottom flask was charged with 14.84 gms (0.038 mole, 1.0 eq.) of 1-bromo-2-cyano-2-(2-chloro-6-fluorophenyl)-4-(4-chlorophenyl)butane in 50 ml of DMSO. To the reaction was added 4.89 gms (0.0457 mole) of Ktriazole in 30 ml of DMSO and the flask was heated to 120° C. After 1.5 hours at 120° C., gas liquid chromatography indicated that the reaction was complete and was quenched by cooling to room temperature and adding 50 ml of water and 250 ml of ethyl acetate. After separating, the organic phase was washed twice with 100 ml of water, concentrated and triturated with ether. The solid was filtered and the filtrate concentrated and triturated with ether. The additional solid was filtered and a total of 8.06 gms was obtained having a melting point of 98°–99° C. (54.6% yield).

IR (nujol, cm$^{-1}$): 3020(m), 1600(s), 1570(m), 1500(s), 1450(s), 1275(s), 1240(m), 1205(m), 1135(m), 910(m), 890(s) and 790(s).

NMR (90 MHz): 2.4–3.2(m, 4H), 4.8–5.2(ABq, 2H), 6.9–7.4(m, 7H), 7.9(s, 1H) and 8.2(s, 1H).

Elemental Analysis: $C_{19}H_{15}N_4FCl_2$: Theor: C: 58.60, H: 3.89, N: 14.40, F: 4.88, Cl: 18.22. Found: C: 58.43, H: 3.91, N: 14.43, F: 4.78, Cl: 17.89.

PREPARATION OF COMPOUND 74

Alpha-[2-(4-bromophenyl)ethyl]-alpha-(2-ethoxyphenyl)-1,2,4-triazole-1-propanenitrile Step 1—Preparation of alpha-[2-(4-bromophenyl)ethyl]-2-ethoxyphenylacetonitrile A 4 neck 1 liter round bottom flask was charged with 5.6 gms of 60% NaH (0.14 mole, 1.4 eq.), washed three times with 25 ml hexanes, in 100 ml of 2:1 toluene:DMF. Then 16.1 gms (0.10 mole, 1.0 eq.) of 2-ethoxybenzylcyanide in 200 ml of 2:1 toluene:DMF was added and stirred at room temperature for 2 hours. After this time, 5.7 gms of KH (0.05 mole, 0.5 eq.) washed with 25 ml of hexanes, in 50 ml of 2:1 toluene:DMF was added. After an additional 1 hour, 31 gms (0.11 mole, 1.1 eq.) of 4-bromophenethyl methanesulfonate in 100 ml of 2:1 toluene:DMF was added dropwise over 10 minutes. The reaction was stirred overnight at room temperature. The reaction was 81% monoalkylated product as indicated by gas liquid chromatography. The reaction was quenched with 10% HCl and 400 ml of ether was added and washed four times with 150 ml of water. The solvent was dried over magnesium sulfate then concentrated and gave 37 gms of a crude orange oil from which a solid crystallized out and was filtered and washed with cold toluene. 14.8 gms of a white solid resulted (43.7% yield).

NMR (90 MHz): 1.3–1.5(t, 3H), 2.0–2.3(m, 2H), 2.2–2.9(m, 2H), 3.9–4.2(m, 3H) and 6.8–7.5(m, 8H).

Step 2—Preparation of 1-bromo-2-cyano-2-(2-ethoxyphenyl)-4-(4-bromophenyl)butane A 3 neck 500 ml round bottom flask was charged with 3.5 gms of 100% KH (0.087 mole, 2.0 eq.), washed twice with 25 ml of hexanes, in 25 ml of DMF. At room temperature 14.8 gms (0.044 mole, 1.0 eq.) of alpha-[2-(4-bromophenyl)ethyl]-2-ethoxyphenylacetonitrile in 60 ml of DMF was added dropwise. After 1 hour, $CH_2Br_2$ (0.066 mole, 1.5 eq.) in 40 ml of DMF was added dropwise. The reaction exothermed to 45° C. and was stirred at room temperature for 3 hours after which gas liquid chromatography indicated the reaction was 85% complete. The reaction was stirred overnight at room temperature and then 0.8 gms of 100% KH (0.022 mole, 0.5 eq.) in 20 ml of DMF was added followed by 1.2 gms of $CH_2Br_2$ in 5 ml of DMF. After 1 hour, the reaction was complete. The reaction was quenched by adding 75 ml of 10% HCl followed by addition of 300 ml of ether. After washing four times with 100 ml water, the product was dried and the solvent removed at the rotovap. 18.3 gms of an orange yellow oil resulted (96.8% yield).

NMR (60 MHz): 1.3–1.6(t, 3H), 2.2–2.8(m, 4H), 3.7–4.2(m, 4H) and 6.8–7.6(m, 8H).

Step 3—Preparation of alpha-[2-(4-bromophenyl)ethyl]-alpha-(2-ethoxyphenyl)-1,2,4-triazole-1-propanenitrile A 300 ml 3 neck round bottom flask was charged with 18.3 gms of 1-bromo-2-cyano-2-(2-ethoxyphenyl)-4-(4-bromophenyl)butane (0.43 mole, 1.0 eq.) in 100 ml of DMSO. To the reaction was added at room temperature 5.4 gms of KTriazole (0.050 mole) and the reaction was stirred at 100° C. for 20 hours. Gas liquid chromatography indicated the reaction was complete and the reaction was quenched by adding 10% HCl and ether. The product crystallized out during the extraction and the solvent was reduced in volume and the product was filtered. 11.3 gms of a light tan solid having a melting point of 130°–132° C. was isolated (63% yield).

IR (nujol, $cm^{-1}$): 1590(w), 1265(m), 1245(m), 1135(m), 1030(m) and 750(m).

NMR (60 MHz): 1.4–1.6(t, 3H), 1.9–2.9(m, 4H), 4.0–4.4(q, 2H), 4.9(s, 2H), 6.8–7.4(m, 8H) and 7.8(s, 2H).

Elemental Analysis: $C_{21}H_{21}N_4BrO$: Theor: C: 59.28, H: 4.98, N: 13.18, O: 3.76, Br: 18.80. Found: C: 59.42, H: 5.06, N: 13.12, O: 3.99, Br: 18.60.

PREPARATION OF COMPOUND 83

Alpha-[2-(3-fluorophenyl)-ethyl]-alpha-phenyl-1,2,4-triazole-1-propanenitrile

Step 1—Preparation of 1-(hydroxymethyl)-1,2,4-triazole

A 3 neck 500 ml round bottom flask equipped with condenser and mechanical stirrer was charged with 69.1 gms of triazole (1 mole), 30.1 gms of paraformaldehyde and 1 ml of triethylamine in 250 ml of THF. The reaction was stirred under nitrogen at reflux for 18 hours after which the mixture was concentrated on the rotovap. A white solid resulted which was filtered and washed with ether and gave 96.8 gms of product (97.6% yield) having a melting point of 67°–70° C. The product can be further purified by dissolving in hot acetone, cooling to room temperature, filtering the solid and washing with ether.

Step 2—Preparation of 1-(chloromethyl)-1,2,4-triazole hydrochloride

A 4 neck 1 liter flask equipped with condenser, addition funnel and mechanical stirrer was charged 45 gms of 1-(hydroxymethyl)-1,2,4-triazole (0.464 mole) in 500 ml of THF was heating to 40° C. with vigorous stirring. Then $SOCl_2$ (61 ml, 0.84 mole) was added dropwise maintaining the temperature at 45° C. During the addition, a precipitate formed and the mixture was stirred for an additional 2 hours. The product was filtered, washed three times with ethyl acetate and vacuum dried at room temperature. 67.3 gms of product having a melting point of 118°–130° C. resulted (94.2% yield).

Step 3—Preparation of 2-(3-fluorophenyl)ethanol; reduction of 3-fluorophenylacetic acid via diborane reduction A 2 liter 4 neck flask stirred under nitrogen, equipped with condenser and addition funnel, was charged with 75 gms of 3-fluorophenylacetic acid (0.48 mole) in 100 ml of THF. Then 500 ml of 1M diborane THF complex (0.50 mole) was added dropwise. Upon addition, gas evolved and the reaction was cooled to maintain the temperature below 10° C. After the addition was complete, the reaction was stirred at room temperature until, by thin layer chromatography, the reaction was complete. The reaction was quenched by adding ice water and the product was extracted into ether then washed with 5% NaOH, 5% HCl, water and dried over magnesium sulfate. After concentration, 77.3 gms of a brown oil resulted.

NMR (90 MHz): 2.6(2, 1H), 2.7–2.9(t, 2H), 3.7–3.9(t, 2H) and 6.9–7.4(m, 4H).

Step 4—Preparation of 2-(3-fluorophenyl)ethyl chloride; chlorination of 2-(3-fluorophenyl)ethanol A 500 ml 4 neck round bottom flask stirred under nitrogen, equipped with condenser and addition funnel, was charged with 14.0 gms of 2-(3-fluorophenyl)ethanol (0.1 mole, 1.0 eq.) in 60 ml of toluene. Then 22 ml of $SOCl_2$ (35.9 gms, 0.30 mole, 3.0 eq.) was added dropwise while maintaining the temperature below 15° C. with external cooling. Pyridine (8.7 gms, 1.1 eq.) was added dropwise in 10 ml of toluene. The reaction was stirred overnight at room temperature after which thin layer chromatography indicated the reaction was complete. The mixture was concentrated and the product isolated after adding water, extracting with ether and washing with water. After drying and concentrating, 10.2 gms of an orange oil resulted (64.5% yield).

NMR (60 MHz): 2.9–3.2(m, 2H), 3.5–3.8(m, 2H) and 6.8–7.4(m, 4H).

Step 5—Preparation of alpha-[2-(3-fluorophenyl)ethyl]-phenylacetonitrile

A 3 neck 1 liter round bottom flask was charged with 5.6 gms of 60% NaH (0.140 mole, 1.4 eq.), washed three times with 25 ml hexanes, in 100 ml of 2:1 toluene:DMF. Then 11.7 gms (0.10 mole, 1.0 eq.) of benzyl cyanide in 150 ml of 2:1 toluene:DMF was added and stirred for 2 hours. Then 2-(3-fluorophenyl)ethyl chloride (20 gms, 0.126 mole) in 100 ml of 2:1 toluene:DMF was added. The reaction was complete after 3 hours, then quenched with 10 ml of 10% HCl. Water was added and extracted with 300 ml of ether which was washed four times with 100 ml of water, then dried and concentrated. 22.5 gms of crude product resulted which was distilled under reduced pressure. 11.2 gms of product having a boiling point of 160°–163° C. at 1 mm Hg resulted (46.9% yield).

NMR (90 MHz): 2.0–2.3(m, 2H), 2.6–2.8(m, 2H), 3.6–3.8(t, 1H) and 6.8–7.5(m, 9H).

Step 6—Preparation of alpha-[2-(3-fluorophenyl)ethyl]-alpha-phenyl-1,2,4-triazole-1-propanenitrile A 500 ml 4 neck round bottom flask was charged with 0.3 gms of 60% NaH (0.075 mole, 3.0 eq.), washed twice with 25 ml of hexanes, in 50 ml of DMF. To the reaction was added dropwise 6.0 gms of alpha-[2-(3-fluorophenyl)ethyl]-phenylacetonitrile (0.025 mole, 1.0 eq.) in 20 ml of DMF. After 1 hour, 6.0 gms of chloromethyltriazole.HCl (0.038 mole, 1.5 eq.) was added directly in two portions. After 1 hour, gas liquid chromatography indicated the reaction was incomplete and an additional 1.5 gms (1.5 eq.) of 60% NaH was added in 25 ml of DMF after washing with 25 ml of hexanes. The reaction was complete in 1 hour and then quenched by adding ether containing methanol. Then 25 ml of 10% HCl was added, followed by 300 ml of ether. Washing four times with water (150 ml) was followed by drying and concentrating to give 5 gms of a yellow oil. The product crystallized out of ether and gave 2.3 gms of product having a melting point of 100°–101° C. (29% yield).

IR (nujol, cm$^{-1}$): 1580(w), 1265(m) and 1140(m).

NMR (90 MHz): 2.2–2.8(m, 4H), 4.6(d, 2H), 6.8–7.6(m, 9H) and 7.8–7.9(d, 2H).

Elemental Analysis: $C_{19}H_{17}N_4F$; Theor: C: 71.21, H: 5.35, N: 5.94, F: 17.50. Found: C: 71.20, H: 5.36, N: 5.93, F: 17.44.

PREPARATION OF COMPOUND 88

Alpha-[2-(3-bromophenyl)ethyl]-alpha-(2-ethoxyphenyl)-1,2,4-triazole-1-propanenitrile Step 1—Preparation of 2-(3-bromophenyl)ethanol; reduction of 3-bromophenylacetic acid via diborane reduction A 2 liter 4 neck flask stirred under nitrogen, equipped with condenser and addition funnel, was charged with 75 gms of 3-bromophenylacetic acid (0.34 mole), in 100 ml of THF. Then 350 ml of 1M diborane-THF complex (0.35 mole) was added dropwise. Upon addition, gas evolved and the reaction was cooled to maintain the temperature below 10° C. After the addition was complete, the reaction was stirred at room temperature until, by thin layer chromatography, the reaction was complete. The reaction was quenched by adding ice water and the product was extracted into ether then washed with 5% NaOH, 5% HCl, water and dried over magnesium sulfate. After concentration, 77.4 gms of product resulted and was chlorinated directly.

NMR (90 MHz): 2.7–2.9(m, 3H), 3.7–3.9(t, 2H) and 7.1–7.4(m, 4H).

Step 2—Preparation of 2-(3-bromophenyl)ethyl chloride; chlorination of 2-(3-bromophenyl)ethanol A 500 ml 3 neck round bottom flask stirred under nitrogen, equipped with condenser and addition funnel, was charged with 20.0 gms of 2-(3-bromophenyl)ethanol, (0.1 mole, 1.0 eq.) in 60 ml of toluene. Then 22 ml of $SOCl_2$ (35.9 gms, 0.30 mole, 3.0 eq.) was added dropwise while maintaining the temperature below 15° C. with external cooling. Pyridine (8.7 gms, 1.1 eq.) was added dropwise in 10 ml of toluene. The reaction was stirred overnight at room temperature after which thin layer chromatography indicated that the reaction was complete. The mixture was concentrated and the product isolated after adding water, extracting with ether and washing with water. After drying and concentrating, 14.2 gms of an orange oil resulted (64.2% yield).

NMR (60 MHz): 2.8–3.1(m, 2H), 3.5–3.8(m, 2H) and 7.0–7.3(m, 4H).

Step 3—Preparation of alpha-[2-(3-bromophenyl)ethyl]-2-ethoxyphenylacetonitrile

A 4 neck 1 liter round bottom flask was charged with 3.5 gms of 60% NaH (0.083 mole, 1.4 eq.), washed three times with 25 ml hexanes, in 100 ml of DMF. Then 9.5 gms (0.059 mole, 1.0 eq.) of 2-ethoxybenzyl cyanide in 200 ml of DMF was added and stirred for 2 hours. Then 2-(3-bromophenyl)ethyl chloride (13 gms, 0.059 mole) in 100 ml of DMF was added. The reaction was incomplete after 20 hours and 2.0 gms of 100% KH (0.05 mole) in 25 ml of DMF was added. After four hours, the reaction was complete and then quenched with 10% HCl, extracted with ether, washed with water, dried and concentrated to give 20 gms of a crude oil (97% pure). The product was distilled under reduced pressure and gave 12.3 gms of product having a boiling point of 195°–210° C. at 1 mm Hg (58.9% yield).

NMR (90 MHz): 1.2–1.4(t, 3H), 2.0–2.3(t, 2H), 2.6–2.9(t, 2H), 3.8–4.2(m, 3H) and 6.7–7.4(m, 8H).

Step 4—Preparation of alpha-[2-(3-bromophenyl)ethyl]-alpha-(2-ethoxyphenyl)-1,2,4-triazole-1-propanenitrile A 500 ml 4 neck round bottom flask was charged with 2.8 gms of 100% KH (0.07 mole, 3.0 eq.), washed twice with 25 ml of hexanes, in 50 ml of DMF. To the reaction was added dropwise 8.0 gms of alpha-[2-(3-bromophenyl)ethyl]-2-ethoxyphenyl acetonitrile (0.023 mole, 1.0 eq.) in 100 ml of DMF. After 1 hour, 5.7 gms of chloromethyltriazole.HCl (0.037 mole, 1.6 eq.) was added directly in two portions. After 1 hour, gas liquid chromatography indicated the reaction was incomplete and an additional 2.8 gms (3.0 eq.) of KH was added followed by 1.8 gms (0.5 eq.) of chloromethyltriazole.HCl. After stirring overnight at room temperature, the reaction was complete and quenched by adding a small quantity of MeOH in 100 ml of ether followed by the addition of 10 ml of 10% HCl. Then 200 ml of ether was added then washed four times with 100 ml of water, dried and concentrated to give 7 gms of a crude oil. The product was purified by flash chromatography with 1:1 ethyl acetate:hexane and gave 2.3 gms (24% yield) of a viscous oil.

NMR (60 MHz): 1.4–1.7(t, 3H), 2.1–3.0(m, 4H), 4.0–4.3(m, 2H), 5.0(s, 2H), 6.9–7.4(m, 8H) and 7.8(s, 2H).

Elemental Analysis: $C_{21}H_{21}N_4BrO$:
Theor: C: 59.28, H: 4.98, N: 13.18, O: 3.76, Br: 18.80.
Found: C: 58.40, H: 5.43, N: 11.56, O: 6.30, Br: 17.69.

PREPARATION OF COMPOUND 93

Alpha-[2-(4-methoxyphenyl)ethyl]-alpha-phenyl-1,2,4-triazole-1-propanenitrile

Step 1—Preparation of alpha-[2-(4-methoxyphenyl)ethyl]phenylacetonitrile

A 4 neck 2 liter round bottom flask equipped with thermometer, dropping funnel and mechanical stirrer was charged with 117 gms (1.0 mole, 2.0 eq.) of benzyl cyanide and 115 gms (0.5 mole, 1.0 eq.) of 2-(4-methoxyphenyl)ethyl methanesulfonate in 400 ml of DMSO and 200 ml of toluene. The reaction was cooled to 10° C. and 50 gms (0.63 mole, 1.2 eq.) of 50% NaOH was added dropwise over 30 minutes. The reaction exothermed to 35° C. and was cooled to 10° C. The reaction was stirred for 48 hours at room temperature and gas liquid chromatography indicated 60% product and 40% benzyl cyanide. The reaction was quenched by adding to 2 liters of water, then extracted three times with ether (1 liter), washed twice with water (1 liter) and brine (1 liter). Drying over $MgSO_4$ and concentrating gave 171 gms of crude oil (67% product). The product was distilled under vacuum and afforded 104 gms of yellow oil (82.5% yield based on mesylate) having a boiling point of 165°–170° C. at 2 mm Hg.

NMR (60 MHz): 1.9–2.4(m, 2H), 2.5–2.7(m, 2H), 3.7(s, 4H), 6.8–7.2(ABq, 4H) and 7.5(s, 5H).

Step 2—Preparation of 1-bromo-2-cyano-2-phenyl-4-(4-methoxyphenyl)butane

A 4 neck 1 liter round bottom flask was charged with 100 grams (0.40 mole, 1.0 eq.) of alpha-[2-(4-methoxyphenyl)ethyl]phenylacetonitrile and 139.1 gms of dibromomethane in 200 ml of DMSO. To the reaction was added 79.6 gms of 50% NaOH (0.99 mole, 2.5 eq.) dropwise over 15 minutes. The reaction exothermed to 95° C. then was cooled to 50° C. and stirred for 1 hour at 50° C. When gas liquid chromatography indicated the reaction was complete, the reaction product was poured into 2 liters of water, extracted three times with ether (500 ml), washed with water (1 liter), brine and dried over sulfate. 130 gms (94% yield) of product as an amber oil resulted after concentrating. The product was used directly in the triazole coupling.

NMR (60 MHz): 2.4–2.8(m, 4H), 3.7(s, 2H), 3.8(s, 3H), 6.8–7.3(ABq, 4H) and 7.5–7.8(br s, 5H).

Step 3—Preparation of alpha-[2-(4-methoxyphenyl)ethyl]-alpha-phenyl-1,2,4-triazole-1-propanenitrile A 1 liter 3 neck flask was charged 57 gms of triazole (0.74 mole, 2.0 eq.) in 300 ml of DMSO and 102 gms of $K_2CO_3$ (0.74 mole, 4.0 eq.). The reaction was stirred at 135° C. for 1 hour after which 127 gms of 1-bromo-2-cyano-2-phenyl-4-(4-methoxyphenyl)butane (0.37 mole, 1.0 eq.) in 200 ml of DMSO was added. The temperature dropped to 115° C. and was heated at 135° C. for 2 hours then at 80° C. for 18 hours. The reaction was poured into water (3 liter), extracted five times with ethyl acetate (500 ml), washed twice with water (500 ml) and 500 ml of brine. After drying over sulfate, filtering and concentrating gave a yellow oil which was slurried in hexane. A yellow solid formed which was filtered with 10% diethyl ether/90% hexanes. Drying yielded 95 gms of a product having a melting point of 91°–94° C. (77.4% yield).

NMR (60 MHz): 2.4–2.9(m, 4H), 3.9(s, 3H), 5.1(s, 2H), 6.8–7.4(ABq, 4H), 7.7–7.9(br s, 5H), 8.2(s, 1H) and 8.4(s, 1H).

Elemental analysis: $C_{20}H_{20}N_4O$:
Theor: C: 72.24, H: 6.06, N: 16.87, O: 4.82.
Found: C: 72.55, H: 6.39, N: 16.09, O: 5.21.

The compounds of the present invention were tested for activity against a number of diseases. The test compounds were dissolved in acetone, methanol and water to form a series of dilutions from 300 ppm to 5 ppm. Depending on when the tests were run, various serial dilutions were used, e.g., 300, 75, 19, 5 or 100, 25, 6. Unless otherwise indicated the plants were sprayed to run-off with a mechanical sprayer the same day or the day before innoculation. The protocol for Wheat Stem Rust (WSR), Wheat Leaf Rust (WLR), Wheat Powdery Mildew (WPM) and Rice Blast (RB) were as follows:

WHEAT STEM RUST (WSR)—*Puccina graminis*

Wheat seedlings cultivar TYLER were grown in redi-earth and used for screening about seven days after planting. The seedlings were fertilized with LIQUID-M* fertilizer prior to use to maintain vigorous plants throughout the testing period.

* LIQUID-M is a trademark of Universal Chemical Co.

Depending on when the test was run one of three methods was used to prepare the urediospore suspensions:

1. Water/Devilbiss Atomizer: A spore suspension of WSR was prepared by harvesting infected leaves from two to three week old culture plants and shaking the leaves vigorously with water plus TWEEN 80** surfactant. The spore suspension was filtered through cheesecloth to remove debris and adjusted to three to five spores per large square on a hemocytometer. The inoculum was applied to plants by using a Devilbiss atomizer. While the plants were still wet, they were placed in a humidity cabinet.

** TWEEN 80 is a trademark of Fisher Scientific Co.

2. Oil/Devilbiss Atomizer: A spore suspension of WSR and oil was prepared by harvesting spores fresh from infected plants two to three weeks old with a vacuum pump or rust collector or rehydrating frozen spores (from deep freeze) and adding to SOLTROL*** spray oil at a concentration of five mg spores to one ml oil. The inoculum was applied to the plants with a Devilbiss Atomizer making one pass over the plants from all four sides. The plants were allowed to dry about twenty minutes and then placed in a humidity cabinet.

*** SOLTROL is a trademark of Phillips Chemical Co.

3. Oil/Small Special Atomizer: The spore suspension was prepared the same as in method no. 2 except four mg spores per one ml oil was used. The inoculum was then dispensed into gelatin capsules and applied with a vacuum pump. Four passes were made on both sides of the plant for uniformity. The plants were allowed to dry about twenty minutes and then were placed in a humidity cabinet.

The humidity cabinet supplied 100% free water and was maintained at a constant temperature of 70° F. The inoculated plants were subjected to twelve hours of darkness followed by three to four hours of fluorescent light. The plants were then transferred into the greenhouse and evaluated thirteen days later.

WHEAT LEAF RUST (WLR)—*Puccinia recondita*

The same procedures used for WSR were used for WLR except that for WLR there was no light requirement.

WHEAT POWDERY MILDEW (WPM)—*Erysiphe graminis*

Wheat seedlings cultivar VICTORY 283 were grown in redi-earth. The seedlings were six to seven days old and were fertilized with LIQUID-M fertilizer before use to promote vigorous growth throughout the test period.

The seedlings were inoculated by shaking sporulating culture plants over them, disseminating mildew spores. The inoculated seedlings were placed in subirrigation trays in a controlled temperature room which provided a 70° F. environment for disease development.

Since WPM development is greatly affected by volatile chemicals, the pots were spread out as much as possible and the trays are separated according to dose by plastic sheets. Disease development was rated seven to ten days after inoculation on a percent control basis.

RICE BLAST (RB)—*Pricularia oryzae*

Seedlings of the rice cultivar M-201 were grown in a greenhouse at 20°-30° C. in 2-inch pots containing unsterilized soil and Turf-Builder* soil/fertilizer for 14 days. The rice plants were not trimmed before use.
* Turf-Builder is a trademark of Scotts Company.

Inoculum was produced in-vitro on oatmeal agar (50 g Gerber** baby oatmeal, 20 g bacto agar, 10 g bacto dextrose, 100 ml deionized water). The plates were inoculated with a mycelial plug (7-14 days old) of *Piricularia oryzae*. The outer edge of the dark region was used in the transfer. Inoculated plates were maintained at room temperature under constant fluorescent light.
** Gerber is a trademark of Gerber Products Co.

*P. oryzae* plates 10-14 days old were flooded with a solution containing 0.25 g sodium oleate, 2 g gelatin and 100 ml deionized water. The plates were scraped with a rubber policeman to release conidia, filtered through a double layer of cheesecloth and spore suspension adjusted to 25,000-30,000 spores/ml using a hemacytometer.

The spore suspension was sprayed on opposite sides of a double row of rice plants using a hand sprayer. Sufficient inoculum was applied to achieve uniform distribution from soil to tip of rice leaves on opposite sides of each pot (approx. 50 ml/50 pots). The hand sprayer was shook after each pass to keep the solution in suspension.

The inoculated plants were immediately placed in a humidity cabinet at 25° C. for 66 hours prior to moving them to the greenhouse under a plastic tent. The plants were subirrigated but not allowed to stand in water more than 2 hours. The plastic sides of the tent were lifted during work hours and closed at end of day.

After 76 hours under greenhouse conditions the bioassay plants were observed and the percent disease control (as compared to inoculated control) was estimated.

The compounds were tested at different dose rates depending on when the tests were run. The results of the tests are set forth in Table 6 for one dose rate for each compound. If the compound was tested more than once at the dose rate, the average is reported.

TABLE 6

| | FUNGICIDAL ACTIVITY | | | |
|---|---|---|---|---|
| | WSR | WLR | WPM | RB |
| | % Control at 300 ppm | | | |
| 1 | 100 | 95 | 99 | 66 |
| 2 | 97 | 100 | 93 | 83 |
| 3 | 100 | 100 | 99 | 98 |
| 4 | 100 | 100 | 100 | 91 |
| 5 | 92 | — | 99 | 15 |
| 6 | 100 | 100 | 96 | 12 |
| 7 | 100 | — | 100 | 88 |
| 8 | 100 | — | 90 | 95 |
| 9 | 100 | — | 97 | 50 |
| 10 | 100 | 100** | 98 | 97 |
| 11 | 100 | 100** | 99 | 100 |
| 12 | 100 | — | 90 | 88 |
| 13 | 94 | — | 99 | 99 |
| 14 | 100 | — | 100 | 100 |
| 15 | 92 | — | 70 | 80 |
| 16 | 100 | 100** | 99 | 100 |
| 17 | 98 | — | 100 | 93 |
| 18 | 100 | — | 100 | 100 |
| 19 | 99 | 100** | 100 | 97 |
| 20 | 95 | — | 100 | 85 |
| 21 | 100 | — | 100 | 63 |
| 22 | 100 | — | 100 | 50 |
| | % Control at 200 ppm | | | |
| 23 | 100 | — | 90 | 0** |
| 24 | 100 | 100*** | 100 | 40** |
| 25 | 100 | 100*** | 100 | 50** |
| 26 | 100 | 100*** | 90 | 83** |
| 27 | 100 | — | 90 | 100 |
| 28 | 100 | — | 100 | 0** |
| 29 | 100 | 95** | 100 | 90** |
| 30 | 100 | 98*** | 100 | 60 |
| 31 | 100 | 95* | 100 | 0 |
| 32 | 100 | 91*** | 100 | 80 |
| 33 | 100 | 91*** | 100 | 0 |
| 34 | 100 | — | — | 100 |
| 35 | 100 | — | — | 100 |
| 36 | 100 | — | 100* | 87 |
| 37 | 100 | 91*** | 100 | 80 |
| 38 | 100 | — | 100 | 0 |
| 39 | 100 | — | 100 | 0 |
| 40 | — | 100 | 100 | 80 |
| 41 | — | 100 | 100 | 0 |
| 42 | 99** | 95 | 100 | 0 |
| 43 | — | 100 | 100 | 0 |
| 44 | 100** | 99 | 100 | 95 |
| 45 | — | 99 | 100 | 50 |
| 46 | — | 75 | 75 | 50 |
| 47 | 100** | 75 | 95 | 50 |
| 48 | — | 75 | 75 | 0 |
| 49 | 100** | 95 | 99 | 0 |
| 50 | 100** | 75 | 100 | 0 |
| 51 | — | 75 | 100 | 50 |
| 52 | — | 50 | — | 90 |
| 53 | — | 95 | 95 | 90 |
| 54 | — | 95 | 95 | 80 |
| 55 | — | 95 | 100 | 80 |
| 56 | — | 99 | 99 | 100 |
| 57 | — | 50 | 50 | 0 |
| | % Control at 100 ppm | | | |
| 58 | — | 0 | 75 | 0 |
| 59 | — | 75 | 95 | 80 |
| 60 | — | 0 | 75 | 0 |
| 61 | — | 0 | 85 | 40 |
| 62 | — | 75 | 95 | 0 |
| 63 | — | 50 | 75 | 0 |
| 64 | 100 | 99 | 87 | 50 |
| 65 | 100 | 95 | 97 | 90 |
| 66 | — | 75 | 95 | 90 |
| 67 | 95 | 99 | 85 | 85 |
| 68 | 95 | 95 | 99 | 85 |
| 69 | 100 | 99 | 100 | 87 |
| 70 | — | 50 | 95 | 80 |
| 71 | 91 | 50 | 99 | 90 |

TABLE 6-continued

| | FUNGICIDAL ACTIVITY | | | |
|---|---|---|---|---|
| | WSR | WLR | WPM | RB |
| 72 | 97 | 0 | 97 | 92 |
| 73 | — | 0 | 85 | 50 |
| 74 | 100 | 92 | 100 | 0 |
| 75 | 100 | 90 | 100 | 0 |
| 76 | 100 | 95 | 100 | 0 |
| 77 | 100 | 50 | 98 | 93 |
| 78 | 99 | 75 | 99 | 100 |
| 79 | 95 | 75 | 85 | 95 |
| 80 | 100 | 99 | 99 | 0 |
| 81 | 100 | 75 | 99 | 0 |
| 82 | 100 | 0 | 95 | 50 |
| 83 | — | 75 | 99 | 98 |
| 84 | 100 | 99 | 99 | 90 |
| 85 | 100 | 99 | 97 | 0 |
| 86 | 100 | 90 | 99 | 85 |
| 87 | 100 | 0 | 100 | 100 |
| 88 | — | 90 | 95 | 0 |
| 89 | 99 | 75 | 99 | 40 |
| 90 | — | 95 | 95 | 0 |
| 91 | 100 | 85 | 95 | 90 |
| 92 | — | 95 | 99 | 0 |
| 93 | 50 | 0 | 99 | 100 |
| 94 | — | 50 | 90 | — |
| 95 | 100 | 97 | 99 | 95 |
| 96 | — | 95 | 97 | — |

*At 100 ppm
**At 150 ppm
***At 75 ppm

The compounds were tested at different dose rates depending on when the tests were run. The results of the tests for the better compounds which were tested are set forth in Table 7 for three rates. If the compound was tested at the same dose rate more than once, the average is reported.

TABLE 7

FUNGICIDAL ACTIVITY

Wheat Stem Rust

| | Compound/Dose Rate (in ppm) | | | | | | |
|---|---|---|---|---|---|---|---|
| | 300 | 200 | 100 | 75 | 33 | 25 | 6 | 5 |
| 1 | 100 | | 100 | | | | | 98 |
| 4 | 100 | | 100 | | | | | 99 |
| 6 | 100 | | 100 | | | | | 100 |
| 10 | 100 | | 100 | | | | | 99 |
| 16 | 100 | | 100 | | | | | 99 |
| 22 | 100 | | 100 | | | | | 95 |
| 23 | | 100 | | | 100 | | 100 | |
| 24 | | 100 | | | 100 | | 90 | |
| 25 | | 100 | | | 100 | | 100 | |
| 26 | | 100 | | | 100 | | 100 | |
| 27 | | 100 | | | 100 | | 100 | |
| 33 | | 100 | | | 100 | | 100 | |
| 37 | | 100 | | | 100 | | 100 | |
| 78 | | | 99 | | | 100 | 100 | |
| 85 | | | 100 | | | 100 | 100 | |
| 86 | | | 100 | | | 100 | 100 | |
| 95 | | | 100 | | | 100 | 99 | |

Wheat Leaf Rust

| | Compound/Dose Rate (in ppm) | | | | | | |
|---|---|---|---|---|---|---|---|
| | 150 | 100 | 75 | 38 | 25 | 19 | 6 | 5 |
| 10 | 100 | | | 100 | | | | 96 |
| 11 | 100 | | | 100 | | | | 94 |
| 16 | 100 | | | 100 | | | | 100 |
| 19 | 100 | | | 100 | | | | 100 |
| 24 | | 100 | | | | 99 | | 97 |
| 25 | | 100 | | | | 99 | | 93 |
| 26 | | 100 | | | | 99 | | 90 |
| 28 | | | | | 95(20) | | | 95 |
| 41 | | 95 | | | | 97 | | 80 |
| 49 | 95 | | | | 95 | | 75 | |
| 69 | 99 | | | | 95 | | 85 | |
| 80 | 99 | | | | 97 | | 95 | |

(20)Compound 28 was tested at 20 ppm

TABLE 7-continued

FUNGICIDAL ACTIVITY

Wheat Powdery Mildew

| | Compound/Dose Rate (in ppm) | | | | | | |
|---|---|---|---|---|---|---|---|
| | 300 | 200 | 100 | 38 | 33 | 25 | 6 | 5 |
| 1 | 99 | | | 99 | | | | 98 |
| 2 | 100 | | | 99 | | | | 98 |
| 4 | 100 | | | 100 | | | | 97 |
| 10 | 98 | | | 97 | | | | 95 |
| 19 | 100 | | | 100 | | | | 96 |
| 28 | | 100 | | | | 100 | | 90 |
| 29 | | 100 | | | | 100 | | 95 |
| 30 | | 100 | | | | 100 | | 100 |
| 31 | | 100 | | | | 100 | | 95 |
| 36 | | | 100 | | | 100 | | 95 |
| 41 | | 100 | | | | 95 | | 95 |
| 49 | | | 100 | | | 100 | | 75 |
| 76 | | | 100 | | | 99 | | 97 |
| 81 | | | 99 | | | 92 | | 92 |
| 82 | | | 95 | | | 97 | | 90 |
| 83 | | | 99 | | | 97 | | 97 |
| 85 | | | 97 | | | 95 | | 95 |
| 86 | | | 99 | | | 99 | | 96 |
| 87 | | | 100 | | | 95 | | 97 |
| 88 | | | 95 | | | 95 | | 95 |
| 94 | | | 90 | | | 95 | | 90 |
| 95 | | | 99 | | | 94 | | 96 |

Rice Blast

| | Compound/Dose Rate (in ppm) | | |
|---|---|---|---|
| | 300 | 75 | 5 |
| 7 | 88 | 85 | 80 |
| 17 | 93 | 99 | 78 |
| 18 | 100 | 100 | 85 |

The activity of a number of the compounds of the present invention was tested against Peanut Cercospora (PC), Barley Helminthosporium (BH) and Wheat Septoria Nodorum (SNW). The protocol for these tests was as follows:

PEANUT CERCOSPORA OR PEANUT EARLY LEAFSPOT (PC)—*Cercospora arachidicola*

Cercospora arachidicola was cultured on peanut-oatmeal agar (POA) in petri plates for 14 days under fluorescent lights that were 20 cm above the cultures. The petri plates were inoculated with 0.5 ml of a spore suspension made in sterile water containing a few drops of Tween 80. The spore suspension was subsequently spread over the surface of the POA plate by means of a sterile glass rod bent in the form of a hockey stick. Spores were harvested from the plates by adding deionized water containing a small amount of Tween 80 to the POA plates. The agar surface was scraped with a rubber policeman or similar blunt object. The spore suspension was filtered through cheesecloth to remove mycelial and agar fragments and then adjusted to a concentration of $2-4 \times 10^5$ spores per ml.

Fourteen day old TAMNUT 74 peanut plants were inoculated by spraying the leaves with inoculum until a uniform film of inoculum was observed on the plant. The inoculated plants were incubated in a humid environment at 85°–90° F. for 72 hours. The plants were removed from the humid environment, allowed to dry, and placed in a greenhouse. Treatment comparisons were made 10–14 days after inoculation.

BARLEY HELMINTHOSPORIUM or BARLEY SPOT BLOTCH TEST (BH)—*Helminthosporium sativum*

Seven day old HENREY barley seedlings in 2" pots were trimmed 24 hours prior to chemical application to provide a uniform plant height and to facilitate uniform inoculation. The plants were sprayed with the test compound via a settling tower (1.1 ml of the desired concentration for each spray). The spray was allowed to settle in the tower for one minute before removing the plants from the tower. After spraying, the plants were allowed to dry for at least 2 hours in a drying hood before inoculation.

The Helminthosporium sativum culture used for inoculum was about 3 weeks old, deep black and sporulating. Five ml of deionized water was added to each Petri dish of culture and the spores were scraped off into the water with a rubber policeman. After scraping, the water was filtered through cheesecloth to remove mycelia and agar pieces. One drop of TWEEN 80 surfactant was added to each 100 ml of spore suspension. The spore concentration was adjusted to 25 spores/ml. Inoculum was applied using a hand sprayer. The inoculated plants were put into a greenhouse after sitting in a humidity cabinet at about 70° F. for 24 hours. The plants were allowed to sit in the greenhouse for 6 days prior to scoring the test. The disease was assessed according to "A MANUAL OF ASSESSMENT KEYS FOR PLANT DISEASES" by Clive James (Key No 1.6.1)

WHEAT GLUME BLOTCH (SNW)—*Septoria nodorum*

The inoculum was produced by placing pieces of sporulating mycelium from 3 week old plates on Czapek-Dox V-8 plates or placing a piece of sporulating mycelium in a test tube containing 20 ml of sterile deionized water, shaking well and after 5 minutes placing enough liquid spore mixture in a fresh plate to make a fine film over the plate. The plates were incubated for 48 hours at 20° C. in darkness until a white mycelium was observed. Then plates were incubated at 21° C. under continuous fluorescent light for 15-20 days. The mycelium had a pink color at the end of the incubation period.

The sporulating plates were flooded with deionized water. The spores were scraped into the water with a rubber policeman. The flooding and scraping was repeated 2-3 times with each plate. The spore suspension was then filtered with cheesecloth. The final spore concentration was adjusted 150-300 spores/ml. Two drops of TWEEN 80 per 500 ml of spore suspension were added.

LEN wheat plants were inoculated by spraying the leaves with the spore suspension and TWEEN 80 using a hand sprayer after optionally spraying the plants with a light mineral oil lightly and waiting 5 minutes. The inoculated plants were incubated for 72 hours in a humidity cabinet at 20° C. with a photoperiod of 16 hours light/8 hours dark. The plants were then placed in a growth chamber for 7-9 days at 20° C. with a photoperiod of 16 hours light/8 hours dark and then evaluated for percent control.

The compounds were tested at different dose rates depending on when the tests were run. The results of the tests for the better compounds which were tested are set forth in Table 8 for three rates. If the compound was tested at the same dose rate more than once, the average is reported.

TABLE 8
FUNGICIDAL ACTIVITY

Peanut Cercospora

| | Compound/Dose Rate (in ppm) | | |
|---|---|---|---|
| | 300 | 75 | 5 |
| 4 | 100 | 100 | 97 |
| 6 | 100 | 100 | 100 |
| 7 | 100 | 100 | 85 |
| 8 | 98 | 100 | 85 |
| 11 | 100 | 100 | 100 |

Barley Helminthosporium

| | Compound/Dose Rate (in ppm) | | |
|---|---|---|---|
| | 300 | 75 | 5 |
| 3 | 100 | 99 | 87 |
| 10 | 99 | 99 | 84 |
| 11 | 100 | 99 | 76 |
| 16 | 100 | 100 | 96 |
| 19 | 99 | 99 | 100 |
| 25 | 94 | 94 | 94 |
| 26 | 94 | 97 | 86 |

Wheat Septoria Nodorum

| | Compound/Dose Rate (in ppm) | | |
|---|---|---|---|
| | 80 | 20 | 5 |
| 10 | 100 | 100 | 90 |
| 49 | 100 | 100 | 90 |

COMPARATIVE TESTING

Compounds 2 and 10 versus comparative Compounds C2a, C2b and C10

Side by side in vitro comparative testing of Compounds 2, 10, C2a, C2b and C10 were done against *P. herpotrichoides* and *Septoria tritici*. The tests were performed by routine PDA poison agar as follows:

POISON AGAR TEST

Thirty-nine grams of potato dextrose agar (PDA) purchased from Difco was suspended in 1 liter of water. The media was autoclaved at 15 psi for 15 minutes. After autoclaving, the media was allowed to cool for 15 minutes. Then a dilution series was prepared by adding a known amount of fungicide to the molten agar. The fungicide was dissolved in methanol, acetone or DMSO previous to mixing with the agar. The fungi were rated for growth after the following incubation periods:

Pseudocercosporella herpotrichoides—12 days at room temp.

Septoria tritici—14 days at room temp.

The results were reported in millimeters of radius and the $EC_{75}$ was calculated. The $EC_{75}$ values in ppm were as follows:

| Pseudocercosporella | | |
|---|---|---|
| C2a (phenyl) | C2b (benzyl) | 2 (phenethyl) |
| 20 | 12 | 0.6 |
| | C10 (benzyl) | 10 (phenethyl) |
| | 20 | 0.2 |

| *Septoria tritici* | | |
|---|---|---|
| C2a | C2b | 2 |
| 8 | 10 | 0.2 |
| | C10 | 10 |

| -continued | |
|---|---|
| 4 | 0.02 |

Therefore, the compound of the present invention has an $EC_{75}$ at least 20 times less than the corresponding phenyl or benzyl compounds.

Compound 6 versus comparative Compound C6

In vivo side by side comparative testing of Compound 6 and comparative Compound C6 was also performed.

Control of Barley Spot Blotch

High volume sprays in acetone:methanol:water were applied on an overhead mechanical sprayer to Pennrad barley seedlings in 3 inch pots. The $EC_{75}$ values were calculated and are set forth in Table 9 below. As shown, the compound of the present invention has an $EC_{75}$ more than 20 times less than the corresponding benzyl compound when treated the day of inoculation.

Control of Wheat Leaf Rust with Foliar Sprays

The compounds were suspended in acetone:methanol:water and were sprayed to run-off on an overhead mechanical sprayer onto Pennol wheat seedlings in 3 inch pots. The plants were inoculated with aqueous suspensions of urediospores (20,000/ml) of *Puccinia recondita* and were incubated for 24 hours at 70° F. in mist and for a further 7 days in a greenhouse. The $EC_{75}$ values were calculated and are set forth in Table 9 below.

Control of Wheat Powdery Mildew with Foliar Sprays

Routine foliar spray using Pennol wheat seedlings in 3 inch pots were performed. The $EC_{75}$ values in ppm were calculated and are set forth in Table 9 below.

TABLE 9

| | Compound 6 (phenethyl) | Compound C6 (benzyl) |
|---|---|---|
| BARLEY SPOT BLOTCH | | |
| Initial (inoculated day of treatment) | 17 | 350 |
| WHEAT LEAF RUST | | |
| Curative (inoculated 1 day before treatment) | 23 | 10 |
| Initial | 15 | 5 |
| WHEAT POWDERY MILDEW | | |
| Initial | 1 | 4 |

As can be seen from the above data, the compound of the present invention clearly controls barley spot blotch better than the comparative compound. Although Compound 6 of the present invention is not one of the better compounds against wheat leaf rust or wheat powdery mildew and the strength of the benzyl series is against the wheat fungi, compound 6 is only somewhat poorer in controlling wheat leaf rust than the comparative benzyl compound and Compound 6 is better against wheat powdery mildew when inoculated on the day of treatment.

Compound 10 versus comparative Compound C10

Control of Wheat Powdery Mildew and Wheat Leaf Rust

On two occasions in vivo side by side comparative testing of Compound 10 and comparative Compound C10 was performed using the protocol set forth before Table 6. The results of the two tests are set forth below:

| | WPM | | | WLR | | |
|---|---|---|---|---|---|---|
| | Compound/Dose rate in ppm ai | | | | | |
| | 100 | 25 | 6 | 100 | 25 | 6 |
| | Test 1 | | | | | |
| 10 | 99 | 95 | 95 | 100 | 100 | 99 |
| C10 | 95 | 95 | 85 | 95 | 85 | 85 |
| | Test 2 | | | | | |
| 10 | 100 | 95 | 95 | 100 | 100 | 99 |
| C10 | 100 | 95 | 95 | 95 | 85 | 0 |

Compound 10 is superior to the comparative compound against wheat leaf rust and as good or better than the comparative compound against wheat powdery mildew.

Based on the foregoing comparative tests the phenethyl compounds are overall superior to corresponding benzyl and phenyl compounds. The compounds of the present invention are more than one magnitude better against Wheat Foot Rot (Pseudocercosporella), Wheat Leaf Blotch (*Septoria tritici*) and Barley Spot Blotch (*Helminthosporium sativum*), and generally superior against Wheat Leaf Rust (*Puccinia recondita*) and Wheat Powdery Mildew (*Erysiphe graminis*).

The clear advantage of the phenethyl triazoles of the present invention is their overall superior efficiency against a number of fungi. The preferred compounds of the present invention have good fungicidal activity against Barley Spot Blight, Peanut Early Leafspot and Rice Blast as well as Wheat Leaf Rust and Wheat Stem Rust.

What is claimed is:

1. A compound of the formula

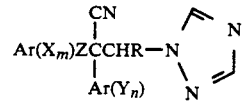

wherein Z is ethylene, ethenylene, ethynylene, isopropylene, halogenated ethylene, halogenated ethenylene or halogenated isopropylene;

$Ar(X_m)$ is a substituted, with $(X_m)$, or unsubstituted $(C_6-C_{10})$ aromatic ring structure;

$Ar(Y_n)$ is a substituted, with $(Y_n)$, or unsubstituted $(C_6-C_{10})$ aromatic ring structure;

each X and Y are independently the same or different and are selected from the group consisting of halogen; $(C_1-C_6)$ alkyl optionally substituted with up to three halogens; $(C_2-C_6)$alkenyl optionally substituted with up to three halogens; hydroxy; $(C_1-C_6)$alkoxy; $(C_2-C_6)$ alkenoxy; phenyl optionally substituted with up to two halogens; cyano; amino; monoalkylamino having up to six carbon atoms; dialkylamino having up to six carbon atoms in each alkyl group; —C(O)H; $(C_1-C_6)$alkylsulfonyl; and —C(O)NR₁R₂ wherein R₁ and R₂ are independently hydrogen or $(C_1-C_6)$alkyl;

R is hydrogen or phenyl optionally substituted with trifluoromethyl, $(C_1-C_6)$alkyl or up to three halogens; and m and n are independently 0 to 3;

and the agronomically acceptable enantiomorphs, acid addition and metal salt complexes thereof.

2. The compound of claim 1 wherein
Z is —$CH_2CH_2$—;
Ar($X_m$) is an optionally substituted phenyl or naphthyl;
Ar($Y_n$) is an optionally substituted phenyl;
X and Y are independently the same or different and are selected from the group consisting of halogen, trifluoromethyl, hydroxy, methoxy, ethoxy, propoxy, methyl, ethyl, phenyl and naphthyl; and
m and n are independently 0, 1 or 2;
and the agronomically acceptable enantiomorphs, acid addition salts and metal salt complexes thereof.

3. The compound of claim 2 wherein
$X_m$ is selected from the group consisting of hydrogen, 2-halogen, 3-halogen, 4-halogen, 3-trifluoromethyl, 4-trifluoromethyl, 4-methoxy, 4-methyl, 4-ethyl and 3,4-halogen; and
$Y_n$ is selected from the group consisting of hydrogen, 2-halogen, 3-halogen, 4-halogen, 2,6-halogen, 3-trifluoromethyl, 2-methoxy and 2-ethoxy;
and the agronomically acceptable enantiomorphs, acid addition salts and metal salt complexes thereof.

4. The compound of claim 2 wherein $X_m$ is hydrogen and the agronomically acceptable enantiomorphs, acid addition salts and metal salt complexes thereof.

5. The compound of claim 4 wherein $Y_n$ is 4-halogen and the agronomically acceptable enantiomorphs, acid addition salts and metal salt complexes thereof.

6. The compound of claim 2 wherein $X_m$ is 4-halogen and the agronomically acceptable enantiomorphs, acid addition salts and metal salt complexes thereof.

7. The compound of claim 6 wherein $Y_n$ is hydrogen or 4-halogen and the agronomically acceptable enantiomorphs, acid addition salts and metal salt complexes thereof.

8. The compound of claim 6 wherein $Y_n$ is 2-halogen and the agronomically acceptable enantiomorphs, acid addition salts and metal salt complexes thereof.

9. The compound of claim 6 wherein $Y_n$ is 2-methoxy or 2-ethoxy and the agronomically acceptable enantiomorphs, acid addition salts and metal salt complexes thereof.

10. The compound of claim 2 wherein $X_m$ is 2-halogen and $Y_n$ is hydrogen or 4-halogen and the agronomically acceptable enantiomorphs, acid addition salts and metal salt complexes thereof.

11. The compound of claim 2 wherein $X_m$ is 3-halogen or 4-halogen and $Y_n$ is 3-halogen and the agronomically acceptable enantiomorphs, acid addition salts and metal salt complexes thereof.

12. The compound of claim 2 wherein $X_m$ is 3-halogen and $Y_n$ is hydrogen, 3-halogen, 4-halogen, 2-methoxy or 2-ethoxy and the agronomically acceptable enantiomorphs, acid addition salts and metal salt complexes thereof.

13. The compound of claim 12 wherein $Y_n$ is hydrogen or 4-halogen and the agronomically acceptable enantiomorphs, acid addition salts and metal salt complexes thereof.

14. The compound of claim 2 wherein $X_m$ is 4-trifluoromethyl and $Y_n$ is hydrogen, 4-halogen, 2-methoxy or 2-ethoxy and the agronomically acceptable enantiomorphs, acid addition salts and metal salt complexes thereof.

15. The compound of claim 2 wherein $Y_n$ is hydrogen and the agronomically acceptable enantiomorphs, acid addition salts and metal salt complexes thereof.

16. The compound of claim 2 wherein $Y_n$ is 4-halogen and the agronomically acceptable enantiomorphs, acid addition salts and metal salt complexes thereof.

17. The compound of claim 2 wherein $Y_n$ is 2-methoxy, 2-ethoxy or 2-propoxy and the agronomically acceptable enantiomorphs, acid addition salts and metal salt complexes thereof.

18. The compound of claim 7 named alpha-[2-(4-chlorophenyl)ethyl]-alpha-phenyl-1H-1,2,4-triazole-1-propanenitrile and the agronomically acceptable enantiomorphs, acid addition salts and metal salt complexes thereof.

19. The compound of claim 7 named alpha-(4-bromophenyl)-alpha-[2-(4-chlorophenyl)ethyl]-1H-1,2,4-triazole-1-propanenitrile and the agronomically acceptable enantiomorphs, acid addition salts and metal salt complexes thereof.

20. The compound of claim 8 named alpha-(2-chlorophenyl)-alpha-[2-(4-chlorophenyl)ethyl]-1H-1,2,4-triazole-1-propanenitrile and the agronomically acceptable enantiomorphs, acid addition salts and metal salt complexes thereof.

21. The compound of claim 9 named alpha-[2-(4-chlorophenyl)ethyl]-alpha-(2-methoxyphenyl)-1H-1,2,4-triazole-1-propanenitrile and the agronomically acceptable enantiomorphs, acid addition salts and metal salt complexes thereof.

22. The compound of claim 13 named alpha-[2-(3-bromophenyl)ethyl]-alpha-phenyl-1H-1,2,4-triazole-1-propanenitrile and the agronomically acceptable enantiomorphs, acid addition salts and metal salt complexes thereof.

23. The compound of claim 14 named alpha-phenyl-alpha-[2-(4-trifluoromethylphenyl)ethyl]-1H-1,2,4-triazole-1-propanenitrile and the agronomically acceptable enantiomorphs, acid addition salts and metal salt complexes thereof.

24. A fungicidal composition for controlling phytopathogenic fungi which comprises an agronomically acceptable carrier and as the active ingredient a fungicidally effective amount of the compound as in any one of claims 1–23.

25. A method for controlling phytopathogenic fungi which comprises of applying to a plant, to plant seed or to a plant habitat, a fungicidally effective amount of the compound as in any one of claims 1–23.

* * * * *

UNITED STATES PATENT AND TRADEMARK OFFICE
CERTIFICATE OF CORRECTION

PATENT NO. : 5,087,635

DATED : February 11, 1992

INVENTOR(S) : Steven H. Shaber

It is certified that error appears in the above-identified patent and that said Letters Patent is hereby corrected as shown below:

At column 2, line 38, "Z" between "or" and "and" should read "2".

Signed and Sealed this

Twentieth Day of April, 1993

Attest:

MICHAEL K. KIRK

*Attesting Officer*     *Acting Commissioner of Patents and Trademarks*